United States Patent [19]
Gustafsson et al.

[11] Patent Number: 6,090,601
[45] Date of Patent: Jul. 18, 2000

[54] SORANGIUM POLYKETIDE SYNTHASE

[75] Inventors: Claes Gustafsson, Belmont; Mary C. Betlach, San Francisco, both of Calif.

[73] Assignee: Kosan Bioscience, Hayward, Calif.

[21] Appl. No.: 09/010,809

[22] Filed: Jan. 23, 1998

[51] Int. Cl.[7] .............................. C12N 9/00; C12N 15/00; C12N 5/00; C12N 1/20; C07H 21/04
[52] U.S. Cl. ...................... 435/183; 435/320.1; 435/325; 435/252.3; 536/23.2
[58] Field of Search ................................ 435/194, 320.1, 435/252.3, 252.33, 183, 325; 536/23.2

[56] References Cited

U.S. PATENT DOCUMENTS

| | | | |
|---|---|---|---|
| 4,551,433 | 11/1985 | DeBoer | 435/253 |
| 4,874,748 | 10/1989 | Katz et al. | 514/29 |
| 5,063,155 | 11/1991 | Cox et al. | 435/76 |
| 5,098,837 | 3/1992 | Beckmann et al. | 435/172.3 |
| 5,149,639 | 9/1992 | Katz et al. | 435/76 |

FOREIGN PATENT DOCUMENTS

| | | |
|---|---|---|
| 0791655 | 8/1997 | European Pat. Off. . |
| WO 93/13663 | 7/1993 | WIPO . |
| WO 95/08548 | 3/1995 | WIPO . |
| WO 96/40968 | 12/1996 | WIPO . |
| 09722711 | 6/1997 | WIPO . |

OTHER PUBLICATIONS

Bollag, D. et al., *Cancer Research* (1995), 55:2325–2333.
Caffrey, P. et al, *FEBS Letters* (1992), 304:225–228.
Dalbie–McFarland, G. et al., *Proc Natl Acad Sci USA* (1982), 79:6409–6413.
Fu, H. et al. *Biochemistry* (1994), 33:9321–9326.
Gerth, K. et al., *Journal of Antibiotics* (1996), 49:560–563.
Geisselsoder, J. et al., *BioTechniques* (1987), 5:786–791.
Jay, E. et al., *J. Bio Chem* (1984), 259:6311–6317.
Kunkel, T.A., *Proc Natl Acad Sci USA* (1985), 82:488–492.
McDaniel, R. et al., *Science* (1993), 262:1546–1550.
Rohr, J., *Angew. Chem. Int. Ed. Engl.* (1995), 34(8):881–888.
Schupp, T. et al., *Journal of Bacteriology* (1995), 177:3673–3679.
Zoller, et al., *Methods in Enzymology* (1983), 100(32):468–501.
Aigle et al., Microbiology, 142, 2815–2824, Jun. 1996.
Cortes et al., Nature, 348, 176–178, Nov. 1990.
Scottie et al., Gene, 130, 65–71, May 1993.
Schwecke et al., PNAS U.S.A., 92, 7839–7843, Aug. 1995.

*Primary Examiner*—Robert A. Wax
*Assistant Examiner*—M. Monshipouri
*Attorney, Agent, or Firm*—Kevin Kaster; Kate H. Murashige; Carolyn Favorito

[57] ABSTRACT

Domains of epothilone polyketide synthase, and polynucleotides encoding therefor. Additionally, chimeric polyketide synthases that include domains, or subsets of domains, patterned on epothilone polyketide synthase. Methods to prepare epothilone in pharmaceutically useful quantitites are described, as are methods to prepare polyketide combinatorial libraries.

24 Claims, 13 Drawing Sheets

```
epo:   EFITGGTGTL GALVARRLVD RHGVKHLVLL SRRGPDAPGA SDLAAELQAR GASVVVAAAD
sor1:  LLITGGTGAA GAHVARWLAR EGAEHLVLIS RRGAQAEGAS ELHAELTALG ARVTFAACDV
sor2:  VLITGGTGTL GALVARRLVV NHDAKHLLLT SRQGASAPGA DVLRSELEAL GASVTLAACD
ery1:  VLVTGGTGGV GGQIARWLAR RGAPHLLLVS RSGPDADGAG ELVAELEALG ARTTVAACDV epo:   AADRVALERV LLAIPHDRPL TAVVHAAGTL DDGVLSSMTP ARLSAVLRAK VDAAVNLDEQ
sor1:  ADRSAVATLL EQLDAEGSQV RAVFHAGGIG RHAPLAATSL MELADVVSAK VLGAGNLHDL
sor2:  VADPRALKDL LDNIPSAHPV AAVVHAASVL DGDLLGAMSL ERIDRVFAPK IDAAWHLHQL
ery1   TDRESVRELL GGIGDDVPLS AVFHAAATLD DGTVDTLTGE RIERASRAKV LGARNLHELT epo:   TRHSPLRAFV LFSSLSGVLG SPAQSNYAAA NAFLDAMG   SEQ ID NO: 1, subset
sor1:  LGPRPLDAFV LFSSIAGVWG GGQQAGYAAG NAFLDALA   SEQ ID NO: 18
sor2:  TQDKPLAAFI LFSSVAGVLG SSGHSNYAAA SAFLDALA   SEQ ID NO: 19
ery1:  RELDLTAFVL FSSFASAFGA PGLGGYAPGN AYLDGLAQ   SEQ ID NO: 20
```

FIG. 1A

```
26-32:      DTACSS SLVSLHLACT ALRQECDLA LTGGVMVITT PAGFV*FSRA RGLARDGRCK
26-35A:      ...... ......... ......... .......... .......... ..........
DEBS KS1:   DTACSS SLVAVHLACQ SLRRGESSLA MAGGVTVMPT PGMLVDFSRM NSLAPDGRCK 26-32:      SFSAQADGVI WSEGCGMLLL KRLSDARRDR DRVLGVIRGS AVNQDRRSQG
26-35A:      FGCQAERARA GPRVAGMLLL KAAV*RAARR RPCAGVIRGS AVNQNVAARF
DEBS KS1:   AFSAGANGFG MAEGAGMLLL ERLSDARRN– GPVLAVLRGT AVNSDGASNG 26-32:      LTAPNGPAQQ RVIRQALSSC GLSPENRRGG  -GAWDGTSLGD PIEAGALAEV
26-35A:     *WRRTALPSS G*SGRALSSC GLSPEDIDAV EAHGTGTSLGD PIEAGALEAV
DEBS KS1:   LSAPNGRAQV RVIQQALAES GLGPADIDAV EAHGTGTRLGD PIEARALFE- 26-32:      FGPERSPERP LYLGSSKSNL GHAQAAAGVA GVIKMVLALQH EVLPKTLHAE
26-35A:     FGPERSPERP LYLGSSKSNL GHAQAAAGVA GVIKMVLSMQH EVLPKTLHAE
DEBS KS1:   -AYGRDREQP LHLGSVKSNL GHTQAAAGVA GVIKMVLAMRA GTLPRTLHAS 26-32:      QPSPHIAWEG SGLSLLQEAR PWRRNGRVRR AGVSSFGISG TNA
26-35A:     QPSPHIGWEG SGLSLLQEAR PWRRNGRVRR AGVSSFGISG TNAH
DEBS KS1:   ERSKEIDWSS GAISLLDEPE PWPAGARPRR AGVSSFGISG TNAH
``` fragment 26-32 corresponds to a subset of SEQ ID NO: 3
fragment 26-35A corresponds to a subset of SEQ ID NO: 5
fragment DEBS KS1 corresponds to SEQ ID NO: 21

FIG.1B

In the preparation of the present patent application, typesetting thereof may have introduced errors into the above-described polynucleotide or amino acid sequences. In that event, reference may be made to the below-listed sequences which are not expected to be subject to any typesetting errors.

for amino acid sequences for SEQ ID NO:5:

Phe-Phe-Gly-Cys-Gln-Ala-Glu-Arg-Ala-Arg-
Ala-Gly-Pro-Arg-Val-Ala-Gly-Met-Leu-Leu-
Leu-Lys-Ala-Ala-Val-Xxx-Arg-Ala-Ala-Arg-
Arg-Arg-Pro-Cys-Ala-Gly-Val-Ile-Arg-Gly-
Ser-Ala-Val-Asn-Gln-Asn-Val-Ala-Ala-Arg-
Phe-Xxx-Trp-Arg-Arg-Thr-Ala-Leu-Pro-Ser-
Ser-Gly-Xxx-Ser-Gly-Arg-Ala-Leu-Ser-Ser-
Cys-Gly-Leu-Ser-Pro-Glu-Asp-Ile-Asp-Ala-
Val-Glu-Ala-His-Gly-Thr-Gly-Thr-Ser-Leu-
Gly-Asp-Pro-Ile-Glu-Ala-Gly-Ala-Leu-Ala-
Glu-Val-Phe-Gly-Pro-Glu-Arg-Ser-Pro-Glu-
Arg-Pro-Leu-Tyr-Leu-Gly-Ser-Ser-Lys-Ser-
Asn-Leu-Gly-His-Ala-Gln-Ala-Ala-Ala-Gly-
Val-Ala-Gly-Val-Ile-Lys-Met-Val-Leu-Ser-
Met-Gln-His-Glu-Val-Leu-Pro-Lys-Thr-Leu-
His-Ala-Glu-Gln-Pro-Ser-Pro-His-Ile-Gly-
Trp-Glu-Gly-Ser-Gly-Leu-Ser-Leu-Leu-Gln-
Glu-Ala-Arg-Pro-Trp-Arg-Arg-Asn-Gly-Arg-
Val-Arg-Arg-Ala-Gly-Val-Ser-Ser-Phe-Gly-
Ile-Ser-Gly-Thr-Asn-Ala-His.

for SEQ ID NO:3:

Asp-Thr-Ala-Cys-Ser-Ser-Ser-Leu-Val-Ser-
Leu-His-Leu-Ala-Cys-Thr-Ala-Leu-Arg-Gln-
Gly-Glu-Cys-Asp-Leu-Ala-Leu-Thr-Gly-Gly-
Val-Met-Val-Ile-Thr-Thr-Pro-Ala-Gly-Phe-
Val-Xxx-Phe-Ser-Arg-Ala-Arg-Gly-Leu-Ala-
Arg-Asp-Gly-Arg-Cys-Lys-Ser-Phe-Ser-Ala-
Gln-Ala-Asp-Gly-Val-Ile-Trp-Ser-Glu-Gly-

FIG.3A

Cys-Gly-Met-Leu-Leu-Leu-Lys-Arg-Leu-Ser-
Asp-Ala-Arg-Arg-Asp-Arg-Asp-Arg-Val-Leu-
Gly-Val-Ile-Arg-Gly-Ser-Ala-Val-Asn-Gln-
Asp-Arg-Arg-Ser-Gln-Gly-Leu-Thr-Ala-Pro-
Asn-Gly-Pro-Ala-Gln-Gln-Arg-Val-Ile-Arg-
Gln-Ala-Leu-Ser-Ser-Cys-Gly-Leu-Ser-Pro-
Glu-Asn-Arg-Arg-Gly-Gly-Gly-Ala-Trp-Asp-
Gly-Thr-Ser-Leu-Gly-Asp-Pro-Ile-Glu-Ala-
Gly-Ala-Leu-Ala-Glu-Val-Phe-Gly-Pro-Glu-
Arg-Ser-Pro-Glu-Arg-Pro-Leu-Tyr-Leu-Gly-
Ser-Ser-Lys-Ser-Asn-Leu-Gly-His-Ala-Gln-
Ala-Ala-Ala-Gly-Val-Ala-Gly-Val-Ile-Lys-
Met-Val-Leu-Ala-Leu-Gln-His-Glu-Val-Leu-
Pro-Lys-Thr-Leu-His-Ala-Glu-Gln-Pro-Ser-
Pro-His-Ile-Ala-Trp-Glu-Gly-Ser-Gly-Leu-
Ser-Leu-Leu-Gln-Glu-Ala-Arg-Pro-Trp-Arg-
Arg-Asn-Gly-Arg-Val-Arg-Arg-Ala-Gly-Val-
Ser-Ser-Phe-Gly-Ile-Ser-Gly-Thr-Asn-Alafor SEQ ID NO:1:

Glu-Phe-Ile-Thr-Gly-Gly-Thr-Gly-Thr-Leu-
Gly-Ala-Leu-Val-Ala-Arg-Arg-Leu-Val-Asp-
Arg-His-Gly-Val-Lys-His-Leu-Val-Leu-Leu-
Ser-Arg-Arg-Gly-Pro-Asp-Ala-Pro-Gly-Ala-
Ser-Asp-Leu-Ala-Ala-Glu-Leu-Gln-Ala-Arg-
Gly-Ala-Ser-Val-Val-Val-Ala-Ala-Ala-Asp-
Ala-Ala-Asp-Arg-Val-Ala-Leu-Glu-Arg-Val-
Leu-Leu-Ala-Ile-Pro-His-Asp-Arg-Pro-Leu-
Thr-Ala-Val-Val-His-Ala-Ala-Gly-Thr-Leu-
Asp-Asp-Gly-Val-Leu-Ser-Ser-Met-Thr-Pro-
Ala-Arg-Leu-Ser-Ala-Val-Leu-Arg-Ala-Lys-
Val-Asp-Ala-Ala-Val-Asn-Leu-Asp-Glu-Gln-
Thr-Arg-His-Ser-Pro-Leu-Arg-Ala-Phe-Val-
Leu-Phe-Ser-Ser-Leu-Ser-Gly-Val-Leu-Gly-
Ser-Pro-Ala-Gln-Ser-Asn-Tyr-Ala-Ala-Ala-
Asn-Ala-Phe-Leu-Asp-Ala-Met-Gly-Ser-

FIG.3B for SEQ ID No:7:

Ala-Leu-Arg-Ala-Trp-Ile-Glu-Arg-Gly-Ala-
Pro-Thr-Pro-Val-Arg-Val-Val-Ile-Asp-Thr-
Asn-Ala-Ala-Ser-Ser-Pro-Arg-Ser-Asp-Val-
Ala-Gly-Ser-Ser-His-Glu-Ala-Thr-Arg-Gln-
Ala-Leu-Ser-Leu-Leu-Gln-Ala-Trp-Leu-Ser-
Glu-Pro-Arg-Leu-Asp-Ala-Val-Xxx-Leu-Val-
Trp-Val-Thr-Arg-Gly-Ala-Val-Ser-Ala-Ala-
Pro-Asp-Asp-Ala-Val-Xxx-Asp-Leu-Ala-His-
Gly-Pro-Leu-Trp-Gly-Leu-Ile-Arg-Thr-Ala-
Arg-Ser-Glu-His-Pro-Glu-Arg-Arg-Leu-Arg-
Leu-Ile-Asp-Val-Gly-Thr-Xxx-Pro-Val-Asp-
Thr-Gly-Leu-Leu-Ala-Xxx-Ala-Leu-Ala-Thr-
Ala-Ala-Glu-Pro-Glu-Leu-Ala-Leu-Pro-Arg-
Gly-Pro-Xxx-Trp-Pro-Pro-Ala-Gly-Ser-Xxx-
Xxx-Pro-His-Arg-Lys-Thr-His-Pro-Thr-Pro-
Arg-Leu-Asp-Leu-Pro-Ala-Pro-Xxx-Cys-Xxx-
Xxx-Asn-Leu-Gly-Arg-Leu-Gly-Xxx-Ala-Xxx-
Asn-Pro-Ser-Cys-Ser-Pro-Xxx-Arg-Val-Xxx-
Ala-Pro-Phe-Ser-Xxx-Leu-Pro-Pro-Gly-Ala-
Xxx-Ser-Pro-Arg-Ala-Pro-Asn-Phe-Ser-Ile-
Leu-Gln-Glu-Xxx-Ala-Pro-Lys-Pro-Phe-Asn-
Val-Ala-Ser-Ile-Phe-Asn-Arg-Lys-Asn-Ser-
Pro-Xxx-Cys-Arg-Ile-Xxx-Pro-Ala-Pro-Leu-
Thr-Val-Leu-Pro-Arg-Xxx-Val-Ser-Xxx-Gly-
Phe-Gln-Thr-Lys-Pro-Thr-Xxx-Cys-Leu-Ala-
Lys-Val-Arg-Ala-Pro-Leu-Xxx-Ile-Thr-Asnfor SEQ ID NO:8:

Thr-Lys-Leu-Arg-Pro-Lys-Pro-Xxx-Xxx-Arg-
Val-Thr-Thr-Gly-Phe-Phe-Val-Gly-Phe-Xxx-
Arg-Lys-Leu-Xxx-Gly-Xxx-Xxx-Gln-Glu-Arg-
His-Xxx-Leu-Glu-Xxx-Asp-Xxx-Ala-Gly-Arg-
Leu-Gly-Lys-Xxx-Ser-Xxx-Leu-Xxx-Lys-Xxx-
Ser-Asn-Arg-Glu-Pro-Trp-Xxx-Xxx-Glu-Val-
Asn-Leu-Gly-Xxx-Arg-Lys-Val-Arg-Ala-Xxx-
Asn-Arg-Val-Phe-Lys-Met-Cys-Cys-Ser-Met-
Gln-His-Glu-Xxx-Leu-Pro-Lys-Thr-Xxx-Arg-
Arg-Ser-Ser-Xxx-Ala-Gly-His-Trp-Trp-Arg-

FIG.3C

Glu-Arg-Ala-Phe-Val-Ala-Ala-Arg-Gly-Ala-
Ser-Val-Ala-Ala-Gln-Arg-Pro-Gly-Ala-Ala-
Arg-Gly-Arg-Val-Val-Val-Arg-Ile-Ser-Gly-
Thr-Asn-Ala-His-Val-Ile-Leu-Glu-Glu-Ala-
Pro-Val-Glu-Ala-Ala-Arg-Glu-Pro-Val-Glu-
Ala-Val-Arg-Glu-Pro-Val-Glu-Ala-Glu-Gly-
Val-Ala-Ile-Pro-Leu-Leu-Leu-Ser-Gly-Arg-
Asp-Glu-Ala-Ser-Val-Ala-Ala-Gln-Ala-Gly-
Arg-Trp-Ala-Lys-Trp-Leu-Glu-Glu-His-Gly-
Glu-Val-Gly-Trp-Ser-Asp-Val-Val-Arg-Thr-
Ala-Ala-Leu-His-Arg-Thr-His-Phe-Glu-Ser-
Arg-Ala-Ser-Val-Leu-Ala-Ala-Ser-Ala-Ala-
Gly-Ala-Val-Glu-Gly-Leu-Arg-Ala-Leu-Ser-
Ser-Gly-Arg-Pro-Asp-Ala-Ala-Val-Val-Ser-
Gly-Thr-Ala-Lys-Arg-Gly-Gly-Lys-Leufor SEQ ID NO:9:

Lys-Leu-Ala-Val-Leu-Phe-Thr-Gly-Gln-Gly-
Ser-Gln-Arg-Leu-Gly-Met-Gly-Lys-Arg-Leu-
Tyr-Glu-Val-Tyr-Pro-Val-Phe-Arg-Ala-Ala-
Phe-Asp-Glu-Val-Cys-Glu-Ala-Leu-Asp-Ala-
His-Leu-Asp-Arg-Gly-Leu-Arg-Xxx-Val-Val-
Phe-Ala-Ala-Ala-Gly-Ser-Glu-Glu-Xxx-Ala-
Gln-Leu-Glu-Arg-Thr-Glu-Tyr-Thr-Gln-Pro-
Gly-Leu-Phe-Ala-Leu-Glu-Val-Ala-Leu-Tyr-
Arg-Gln-Trp-Xxx-Ser-Trp-Gly-Leu-Asn-Pro-
Leu-Arg-Cys-Trp-Gly-Thr-Arg-Xxx-Glu-Xxx-
Xxx-Thr-Leu-Arg-Thr-Xxx-Arg-Val-Xxx-Xxx-
Xxx-Leu-Arg-Thr-Gln-Xxx-Thr-Xxx-Val-Pro-
Pro-Xxx-Ser-Ala-Asp-Gln-Gly-Phe-Gln-Xxx-
Arg-Gly-Thr-Met-Phe-Pro-Xxx-Lys-Pro-Pro-
Asn-Pro-Lys-Xxx-Thr-Gly-Xxx-Ser-Lys-Ser-
Gly-Gln-Gly-His-Xxx-Leu-Pro-Gly-Xxx-Pro-
Pro-Ser-Thr-Ser-Asn-Xxx-Thr-Asn-Ala-Phe-
Xxx-Val-Ala-His-Ala-Glu-Pro-Gly-Arg-Pro-
Pro-Leu-Ser-Phe-Xxx-Leu-Pro-Pro-His-Xxx-
Glu-Xxx-Lys-Ile-Glu-Val-Pro-Ile-Leu-Pro-
Pro-Leu-Arg-Val-Pro-Xxx-Ala-Pro-Cys-Lys-
Thr-Asn-Xxx-Ile-Val-Asp-Xxx-Xxx-Gly-Pro-
Lys-Asn-

FIG.3D

For SEQ ID NO:10:

Gly-Lys-Xxx-Xxx-Xxx-Leu-Val-Lys-Phe-Ala-
Xxx-Ile-Phe-Gly-Asn-Ala-Gly-Gly-Asp-Phe-
Val-Gly-Pro-Asn-Arg-Gly-Gly-Cys-Leu-Val-
Xxx-Xxx-His-Arg-Thr-Gly-Arg-Asn-Xxx-Xxx-
Gly-Gln-Xxx-Glu-Gly-Val-Xxx-Arg-Arg-Thr-
Leu-Pro-Leu-Pro-Gly-Val-Asp-Glu-Leu-Xxx-
Xxx-Ala-His-Ser-Xxx-Xxx-Gly-Gly-Xxx-Asp-
Phe-Ser-Gly-Phe-Thr-Arg-Val-Asp-Glu-Val-
Ile-Arg-Leu-Arg-Pro-Ala-Phe-Gln-Gly-Leu-
Trp-Ser-Xxx-Arg-Xxx-Xxx-Thr-Asp-Phe-Phe-
Arg-Pro-Gly-Val-Phe-Ala-Gln-Arg-Arg-Asp-
Glu-Gln-Arg-Arg-Gly-Leu-Arg-Val-His-Pro-
Ala-Xxx-Met-Asn-Xxx-Ala-Leu-His-Thr-Met-
Phe-Ala-Ala-Phe-Ala-Glu-Val-Ser-Ala-Pro-
Xxx-Asp-Val-Leu-Leu-Xxx-Phe-Ser-Cys-Ser-
Xxx-Val-Ala-Leu-His-Ala-Thr-Gly-Ala-Ser-
Glu-Xxx-Arg-Val-Arg-Leu-Glu-Xxx-Ala-Gly-
Gly-Arg-Asp-Ser-Ala-Gln-Ala-Ala-Ala-Ser-
Leu-Arg-Val-Thr-Asp-Ala-Ala-Gly-Gln-Pro-
Val-Val-Ser-Val-Gly-Ala-Leu-His-Leu-Arg-
Arg-Ala-Thr-Ala-Glu-Gln-Leu-Arg-Ala-Ala-
Thr-His-Ala-Glu-Ala-Gln-His-Leu-Tyr-Arg-
Val-Asp-Phe-Gln-Leu-Val-Ser-Leu-Val-Glu-
Ala-Gly-Ser-Lys-Val-Asp-Ser-Leu-Val-Val-
Leu-Arg-Ala-Pro-Glu-Gly-Arg-Gly-Arg-Leu-
Gly-Glu-Ala-Leu-Gly-Val-Glu-Ala-Ile-Ala-
Gly-Leu-Asp-Alafor polynucleotide sequences for SEQ ID NO:2, including primers:

GAATTCATCACCGGAGGCACCGGCACCCTCGGCGCTCTCGTGGCGCGTCGCCTCGTC
GACCGCCACGGCGTCAAGC
ACCTGGTGCTGCTCTCGCGCCGGGGCCCGGATGCTCCCGGCGCATCCGACCTCGCCG
CGGAGCTCCAGGCGCGCGG
CGCCTCCGTCGTCGTCGCCGCCGCGGACGCTGCCGATCGCGTCGCCCTCGAGCGGGT
GCTGCTCGCCATCCCGCAC
GACAGGCCGCTGACCGCCGTCGTGCACGCCGCAGGCACACTCGACGACGGCGTGCT
CTCCTCGATGACGCCGGCGC

FIG.3E

GCCTGAGCGCCGTGCTCCGGGCCAAGGTCGACGCGGCCGTCAACCTCGACGAGCAG
ACGCGCCACAGCCCGCTGCG
CGCCTTCGTCCTGTTCTCGTCGCTCTCCGGGGTGCTCGGGAGCCCCGCCCAGTCCAA
TTACGCCGCCGCCAACGCC
TTCCTCGACGCCATGGGATCC// for SEQ ID NO:4:

GACACGGCTTGTTCGTCGTCGCTGGTGTCGCTGCACCTGGCGTGCACGGCGCTGCGC
CAGGGCGAATGCGACCTGG
CGCTGACCGGCGGGGTGATGGTGATCACCACCCCCGCGGGATTCGTTTAGTTCAGTC
GTGCCCGGGGGCTTGCGCG
AGACGGTCGGTGCAAGAGCTTCTCTGCCCAGGCTGACGGCGTCATCTGGTCCGAAG
GGTGCGGGATGCTGTTGCTG
AAGCGGCTGTCTGACGCGCGGCGCGACCGCGACCGTGTGCTGGGGGTGATCCGTGG
CTCTGCGGTGAACCAGGACC
GTCGCAGCCAGGGTCTGACGGCGCCGAACGGCCCTGCCCAGCAGCGGGTGATCCGG
CAGGCGCTGTCGTCGTGTGG
TCTGTCGCCCGAGAATCGACGCGGTGGAGGCGCATGGGACGGTACGAGCCTCGGAG
ACCCGATCGAGGCCGGAGCG
CTGGCGGAGGTGTTTGGACCGGAGCGTAGCCCCGAGCGTCCGCTGTACCTGGGGGTC
GTCGAAGTCGAACCTGGGAC
ATGCGCAGGCGGCCGCGGGTGTGGCGGGCGTGATCAAGATGGTGCTGGCGCTGCAG
CACGAGGTGCTGCCGAAGAC
GCTGCATGCGGAGCAGCCGAGCCCGCACATCGCGTGGGAGGGGAGCGGGCTGTCAT
TGCTGCAAGAGGCGCGTCCG
TGGCGGCGCAACGGCCGGGTCCGTCGTGCCGGCGTGTCGTCGTTCGGGATCAGCGG
AACTAACGCCC// for SEQ ID NO:6:

TTCTTCGGTTGCCAGGCGGAACGGGCGCGGGCTGGGCCGAGGGTTGCGGGAATGCT
GTTGTTGAAAGCGGCTGTCT
GACGCGCAGCGCGACGGCGACCGTGTGCTGGGGTGATCCGTGGCTCTGCGGTGAAC
CAGAACGTCGCAGCCAGGTT
CTGATGGCGCCGAACGGCCCTGCCCAGCAGCGGGTGATCCGGCAGGGCGCTGTCGT
CGTGTGGTCTGTCGCCCGAG
GACATCGACGCGGTGGAGGCGCACGGTACGGGCACGAGCCTTGGAGACCCGATCGA
GGCCGGAGCGCTGGCGGAGG
TGTTTGGACCGGAGCGTAGCCCCGAGCGTCCGCTGTACCTGGGATCGTCGAAGTCGA
ACCTCGGACATGCGCAGGC
GGCGGCGGGCGTGGCGGGCGTGATCAAGATGGTGCTGTCGATGCAGCACGAGGTGC

FIG.3F

TGCCGAAGACGCTGCACGCG
GAGCAGCCGAGCCCGCACATTGGGTGGGAAGGAAGCGGGCTGTCGCTGCTGCAAGA
GGCGCGTCCGTGGCGGCGCA
ACGGCCGGGTCCGTCGTGCCGGCGTGTCGTCGTTCGGGATCAGCGGAACTAACGCG
CAC// for SEQ ID NO:11:

ATGCATTGCGCGCTTGGATCGAGCGGGGCGCGCCAACGCCTGTGCGGGTGGTGATC
GACACGAACGCTGCCAGCTC
ACCGCGCTCGGACGTGGCGGGGTCGTCGCACGAGGCGACGAGGCAGGCGCTGTCGC
TGCTGCAAGCGTGGTTGTCG
GAGCCGCGGCTCGACGCTGTCGANCTGGTGTGGGTGACGCGGGGCGCGGTCAGCGC
AGCTCCGGACGACGCCGTCG
ANGACCTGGCGCACGGGCCGCTGTGGGGGCTTATTCGCACGGCGCGCAGCGAGCAC
CCCGAGCGCCGGCTGCGCTT
GATCGATGTGGGGACCGANCCCGTGGACACTGGGCTGCTGGCGCNGGCGCTGGCGA
CGGCGGCGGAACCNGAACTT
GCCCTGCCCCGGGGCCCGTNCTGGCCCCCCGCTGGTTCCNTACNGCCGCACCGAAAA
ACTCACCCAACCCCCCGGC
TGGACCTCCGGCACCTNCTTGTTNACNGAACCTTGGCCGTCTTGGGCNAGCGTNAA
ACCCNTCTTGTTCCCCCNC
NCGGGTTTAAGCACCTTTTTCTNAACTTCCCCCCGGGCCTGAAGCCCCCGGGCCCC
CAACTTTTCAATCCTCCAA
GAAANCGCCCCAAAACCTTCAATGTTGCTTCAATTTTCAACCGGAAAAATTCCCCC
TTNTGCCGGATTAANCCGG
CCCCCCTAACCGTTCTNCCCCGCTNGGTTTCAAANGGTTTTCAAACNAAGCCAACCN
CTTGTTTGGCCAAGGTAAG
GGCNCCCCTCCNAATAACGAACGNTTN for SEQ ID NO:12:

TGNACCAAGCTAAGGCCGAAGCCCNGCANNAGGGTAACNACAGGCTTTTTTGTNGG
TTTTNCCCGAAAATTAANGG
GNGNGGNNCAGGAACGGCACNCCCTNGAANTCGATTGAGCCGGACGNTTGGGGAA
GNTTTCGGNCTTGGNCAAGCN
GAGCAACCGTGAACCTTGGTTNNTGGAAGTGAACCTTGGCANGCGCAAGGTTCGGG
CGGNTAACCGGGTGTTCAAG
ATGTGCTGTTCGATGCAGCACGAGNTGCTGCCGAAGACGTGNAGGCGGAGCAGCNG
AGCCGGNCATTGGTGGAGGG
AGCGGGCTTTCGTTGCTGCAAGAGGCGCGTCCGTGGCGGCGCAACGGCCGGGCGCG
GCGCGCGGGCGTGTCGTCGT

FIG.3G

TCGGATCAGCGGGACGAACGCCCATGTCATCCTCGAAGAGGCGCCGGTGGAGGCGG
CTCGCGAGCCGGTGGAGGCG
GTGCGCGAGCCGGTGGAGGCGGAGGGTGTTGCGATACCGCTGTTGCTGTCGGGGCG
AGACGAGGCCTCGGTGGCGG
CGCAGGCGGGGCGGTGGGCGAAGTGGCTGGAAGAGCACGGGGAGGTGGGGTGGTC
GGACGTGGTGAGGACGGCGGC
GCTGCACCGGACGCACTTCGAGTCGCGGGCGTCGGTGCTTGCGGCGAGCGCTGCGG
GAGCTGTGGAGGGTCTTCGC
GCGCTGTCGTCGGGGCGGCCGGATGCGGCGGTGGTGAGCGGGACGGCGAAGCGAG
GCGGGAAGCTT// for SEQ ID NO:13:

AAGCTTGCGGTGCTGTTCACGGGGCAGGGCAGCCAGCGGCTCGGGATGGGGAAGAG
GCTTTACGAAGTGTACCCCG
TGTTCCGTGCGGCGTTCGACGAGGTGTGCGAGGCGCTGGACGCGCATCTCGACCGTG
GGTTGAGAGANGTGGTGTT
CGCGGCCGCGGGCAGCGAGGAANGAGCGCAGCTGGAGCGGACGGAGTACACGCAG
CCCGGGCTGTTTGCGCTGGAA
GTGGCGCTGTACCGTCAGTGGGANTCGTGGGGGCTGAACCCGCTGCGCTGCTGGGG
CACTCGATANGAAANCTGAA
CGCTGCGCACGTNGCGGGTNTNCTGANCCTTGCGGACGCAGCNAACTANTGTNCCC
CCGCNGTCNGCTGATCAAGG
GTTCCAAGNCCGGGGAACCATGTTTCCGTNGAAGCCTCCGAACCCGAAGTNCACCG
GCNCTTCGAAGTCNGGCCAG
GGCCACNAACTCCCCGGCTAACCCCCATCCACGTCTAACNGGACAAACGCGTTCNC
CGTTGCCCACGCTGAGCCCG
GCCGCCCCCCGCTTTCTTTTTNCCCTTCCACCCCATNACGAACNGAAAATCGAAGTCC
CGATTCTTCCCCCCCTGCG
TGTACCNTANGCACCCTGCAAAACCAATTNCATTGTTGATTNCAANGGCCCCAAGAA
CC for SEQ ID NO:14:

NGGCAAGNGCNGGGNTTTGGTTAAATTCGCCCNTATTTTCGGAAATGCCGGGGGTG
ATTTTGTTGGGCCCAACCGG
GGNGGGTGTTTGGTTNAANACCACCGNACAGGACGGAATNCCCNTGGTCAANAGGA
AGGGGTTTNACGAAGAACCT
TGCCACTTCCGGGAGTTGATGAGCTAANANTTGCCCATTCCNGGCNCGGAGGCGNT
GACTTTTCGGGTTTTACGAG
GGTTGATGAGGTGATTCGGTTACGCCCGGCCTTCCAGGGTTTGTGGAGCTNTCGNNT
CGANACGGACTTTTTTCGC

FIG.3H

CCGGGTGTTTTTGCCCAAAGACGGGACGAACAGCGCCGAGGATTACGGGTGCATCC
GGCGNTGATGAACNCCGCGT
TGCATACGATGTTCGCAGCGTTTGCGGAGGTATCAGCGCCGGANGACGTGCTGCTGC
NTTTTTCGTGTTCGGANGT
GGCGTTGCACGCCACGGGGGCGAGCGAGNTCCGGGTGAGGCTGGAGNTCGCAGGA
GGCAGAGACTCGGCACAGGCA
GCCGCNTCGCTGCGCGTTACAGATGCCGCCGGCCAGCCGGTGGTGAGCGTCGGTGC
CCTGCATCTGCGCCGGGCGA
CGGCCGAGCAGCTGCGGGCAGCGACGCATGCCGAGGCGCAGCACCTGTACCGGGTG
GACTTCCAGCTCGTGAGCCT
CGTGGAGGCGGGCTCGAAGGTGGACTCGCTGGTGGTGCTCCGTGCGCCTGAGGGGC
GAGGGCGACTGGGCGAAGCG
CTGGGTGTGGAGGCGATCGCAGGCCTCGATGCAT

FIG. 3I

Epothilone A: R = H
Epothilone B: R = CH₃

SORANGIUM POLYKETIDE SYNTHASE

FIELD OF THE INVENTION

The present invention relates to polyketide synthase ("PKS") enzymes that are capable of producing epothilone compounds. Epothilone (FIG. 4), is a polyketide antibiotic that also evidences antitumor activity. Epothilone was originally discovered based on antifungal activity identified in the myxobacterium *Sorangium cellulosum* (see K. Gerth et al., *Journal of Antibiotics,* 49, pp. 560–563, 1996). Given that it is difficult to produce such compounds by traditional chemical approaches, and that expression from wild-type myxobacteria is at levels too low for practical commercial use, there has been considerable interest in finding alternate means to produce these compounds. Accordingly, the present invention is directed to the production of PKS enzymes specific for epothilone, to polynucleotides that encode such synthases, and to host cells in which such encoding polynucleotides can be advantageously expressed. Further enhancements in the biological activities of epothilone, through production of derivatives thereof, is also made possible according to the practice of the invention.

A large variety of polyketides having a vide spectrum of useful biological activities are known, and further variations including those generated from combinatorial libraries are possible. As elaborated below, this nearly infinite design flexibility is made possible in part by the modular nature of polyketide synthases, which are actually highly ordered complexes of multiple catalytic domains organized into modules. Accordingly, further aspects of the present invention include, for example, (1) providing encoding DNA for a chimeric PKS that is substantially patterned on a non-epothilone producing enzyme, but which incorporates one or more functional domains of epothilone PKS; (2) providing an encoding DNA for a chimeric PKS that is substantially patterned on the epothilone-producing enzyme, but which includes one or more catalytic domains associated with other PKS species; and (3) the use of combinatorial or other technologies to further enhance the extent of PKS and polyketide libraries.

BACKGROUND OF THE INVENTION

Polyketides represent a large family of diverse compounds synthesized from 2-carbon units through a series of condensations and subsequent modifications. Polyketides occur in many types of organisms including fungi, and mycelial bacteria, in particular the actinomycetes. An appreciation for the wide variety of polyketide structures, and for their biological activities, may be gained upon review of the extensive art, for example, published International Patent Specifications WO 93/13663 and WO 95/08548; U.S. Pat. Nos. 5,098,837, 5,149,639, 4,874,748, 5,063,155; and the journal articles H. Fu et al., *Biochemistry,* 33, pp. 9321–9326, (1994); R. McDaniel et al., *Science,* 262, pp. 1546–1550, (1993); and J. Rohr, *Angew. Chien. Illt. Ed. Engl.* 34(8), pp.881–888, (1995).

Polyketides are synthesized in nature on polyketide synthases ("PKS"). These enyzmes, which are actually complexes of multiple enzyme activities, are in some ways similar to, but in other ways different from, the synthases which catalyze condensation of 2-carbon units in the biosynthesis of fatty acids. Two major types of PKS are known which are very different in their construction and mode of synthesis. These are commonly referred to as Type I or "modular" and Type II "aromatic."

The PKS enzyme complexes that are generally the subject of the present invention, and epothilone-PKS in particular, are members of the group designated Type I or modular PKS. In this type of PKS, a set of separate catalytic active sites (each active site is termed a "domain", and a set thereof is termed a "module") exists for each cycle of carbon chain elongation and modification. Based on the general nature of PKS activities it is possible to determine from the molecular structure of epothilone that epothilone-PKS consists of 8 modules, although the number of polypeptides that provide the modules is unknown, as is the exact nature of the starter unit.

FIG. 9 of aforementioned W095/08548 depicts a typical genetic model for a Type I PKS, in this case for 6-deoxyerythronolide B synthase ("DEBS") involved in the production of erythromycin. Six separate modules, each catalyzing a round of condensation and modification of a 2-carbon unit, are present. The number and type of catalytic domains that are present in each module varies (see the WO FIG. 9) based on the needed chemistry, and the total of 6 modules is provided on 3 separate polypeptides (designated DEBS-1, DEBS-2, and DEBS-3, with 2 modules per each). Each of the DEBS polypeptides is encoded from a separate open reading frame (gene), see Caffrey et al., *FEBS Letters,* 304, pp. 205, 1992.

The catalytic domains of the DEBS polypeptides provide a representative example of Type I PKS design. In this particular case, modules 1 and 2 reside on DEBS-1, modules 3 and 4 on DEBS-2, and modules 5 and 6 on DEBS-3, wherein module 1 is defined as the first module to act on the growing polyketide backbone, and module 6 the last.

The minimal PKS module is typified by module 3 which contains a ketosynthase ("KS") domain, an acyltransferase ("AT") domain, and an acyl carrier protein ("ACP") domain. These three enzyme activities are sufficient to activate the 2-carbon extender unit and attach it to the growing polyketide molecule. Additional domains that may be included in a module relate to reactions other than the actual condensation, and include a ketoreductase activity ("KR") activity, a dehydratase activity ("DH"), and an enoylreductase activity ("ER"). With respect to DEBS-1, the first module thereof also contains repeats of the AT and ACP activities because it catalyzes initial condensation, i.e. it begins with a "loading domain" represented by AT and ACP, which determine the nature of the starter unit. The "finishing" of the 6deoxyerythronolide molecule is regulated by a thioesterase activity ("TE") in module 6. This thioesterase appears to catalyze cyclization of the macrolide ring thereby increasing the yield of the particular polyketide product.

In PKS polypeptides, the regions that encode enzymatic activities (domains) are separated by linker or "scaffold"-coding regions. These scaffold regions encode amino acid sequences that space the enzymatic activities (domains) at the appropriate distances and in the correct order. Thus, these linker regions collectively can be considered to encode a scaffold into which the various domains (and thus modules) are placed in a particular order and spatial arrangement. Generally, this organization permits PKS domains of different or identical substrate specificities to be substituted (usually at the level of encoding DNA) between PKS species by various available methodologies. Thus, there is considerable flexibility in the design of new PKS in order to produce novel polyketide pharmaceuticals.

An additional level of structural complexity in the resultant polyketides may be introduced by subsequent glycosylation or other post-PKS reactions.

SUMMARY OF THE INVENTION

As aforementioned, the polyketide antibiotic epothilone was first discovered based on its activity as an antifungal compound. Forms A and B thereof were isolated (see FIG. 4) differing in whether the R group at position 12 is hydrogen or methyl. It was subsequently determined that epothilone compounds have valuable activities as antitumor agents based on the microtubule stabilization mechanism previously recognized for taxol (see D. Bollag et al., Cancer Research, 55, pp. 2325–2333, 1995). Since epothilones evidence certain advantages over taxol (for example, greater solubility in water and greater efficacy against multi-drug resistant cells), there has been considerable interest in these compounds, and in methods to produce pharmaceutically useful quantities thereof.

In a first embodiment of the present invention, there are provided polynucleotides that comprise an encoding sequence for one or more domains of epothilone polyketide synthase, or a subset thereof. In a preferred example, the polynucleotide also comprises encoding sequence for one or more domains of another polyketide synthase. Expression of such encoding DNAs, typically in suitable host cells, leads to the production of useful quantities of chimeric synthases capable of producing valuable polyketides.

Accordingly, there is provided a chimeric polyketide synthase (PKS) wherein at least 10 consecutive amino acids in one or more domains of one or more modules thereof are derived from one or more domains of one or more modules of epothilone polyketide synthase. Preferably at least 15, and most preferably at least 20 consecutive amino acids are included. Representative epothilone PKS domains useful in this aspect of the invention include, for example, KR, DH, AT, and KS domains. In the usual case, an entire epothilone PKS domain is included in the chimeric PKS.

In the typical practice of the invention, the chimeric PKS is assembled from polypeptides encoded by DNA molecules that comprise encoding sequences for polyketide synthase domains, wherein at least one encoded domain includes at least 10 consecutive amino acids corresponding to a domain of epothilone polyketide synthase. In such DNA molecules the encoding seqeunces are operably linked to control sequences so that expression therefrom in host cells is effective.

Representative examples of amino acid sequences useful in constructing the chimeric PKS of the invention include, for example, the following sequences from epothilone PKS, that is:

SEQ ID NO:1, SEQ ID NO: 3, SEQ ID NO: 5, SEQ ID NO:7, SEQ ID NO: 8, SEQ ID NO: 9 and SEQ ID NO:10.

These and other aspects of the present invention, including use of combinatorial approaches, are described according to the Detailed Description of the Invention, which follows directly.

BRIEF DESCRIPTION OF THE DRAWINGS

FIG. 1, panel A, shows a comparison of the amino acid sequence of certain polyketide ketoreductase (KR) domains (SEQ ID NOS: 18–20) with a region of an epothilone ketoreductase domain (SEQ ID NO:1)

FIG. 1, panel B, shows a comparison of the amino acid sequence from the erythromycin module 1 ketosynthase domain (DEBS KS1 fragment, SEQ ID NO:21) with regions of two epothilone ketosynthase domains (SEQ ID NOS: 3,5).

FIG. 3 (panels A–H) provides an additional representation of the polynucleotide and amino acid sequences disclosed herein (SEQ ID NOS 1–14 as labeled).

DETAILED DESCRIPTION OF THE INVENTION

Figure 2:
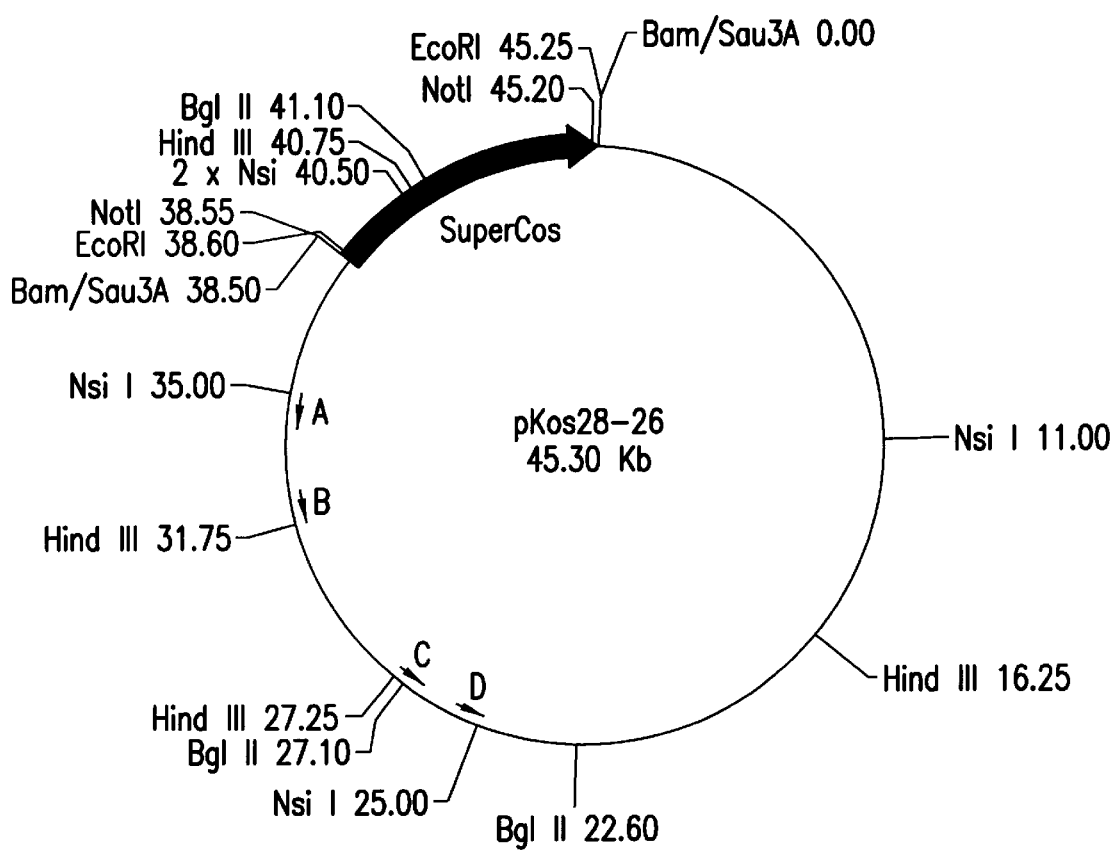
FIG. 2 shows a map of the the 45.3 kb cosmid pKos28-26.
Figure 4:
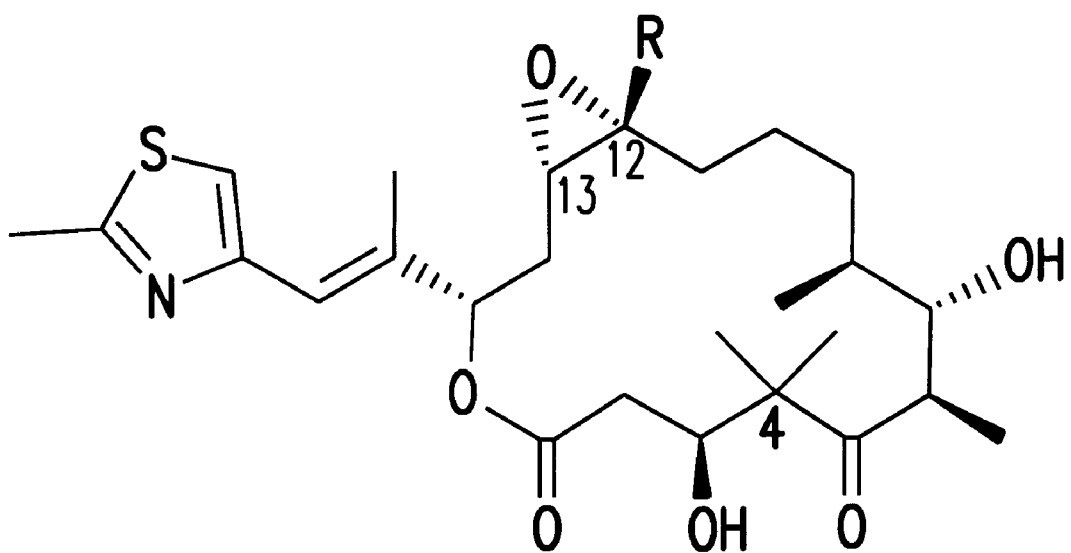
FIG. 4 shows the structure of epothilone A and epothilone B.

Given the valuable pharmaceutical properties of epothilones, it is important to devise means by which pharmaceutically useful quantities thereof can be produced. As aforementioned, only limited quantities of epothilones can be recovered from microbial cells that normally produce such polyketides, and resort to synthetic methods is impractical.

According to the practice of the invention, purified and isolated DNA molecules are provided that comprise one or more encoding sequences for one or more domains of epothilone polyketide synthase. Examples of such encoded domains include epothilone polyketide synthase KR, DH, AT and KS domains as evidenced by the amino acid sequences disclosed herein as SEQ ID NOS: 1, 3, 5 and 7–10. The corresponding encoding sequences are disclosed herein as SEQ ID NOS: 2, 4, 6, and 11–14 respectively.

A further example of an encoding polynucleotide is represented by the complete sequences of cosmid pKos28-26 (see Example 2) that correspond to epothilone polyketide synthase domains and modules.

Upon determination of all of the encoding sequences for the epothilone polyketide synthase complex, and upon elucidation of the organization of domains and modules in the synthase polypeptides, appropriate DNA molecules may be constructed in which the complete set of appropriately arranged epothilone PKS-encoding sequences are operably linked to expression control sequences that are effective in suitable host cells.

Further aspects of the invention include:

(1) providing encoding DNA for a chimeric PKS that is substantially patterned on a non-epothilone producing enzyme, but which incorporates one or more functional domains of epothilone PKS;

(2) providing an encoding DNA for a chimeric PKS that is substantially patterned on the epothilone-producing enzyme, but which includes one or more catalytic domains associated with other PKS species; and (3) the use of combinatorial or other technologies to further enhance the extent of PKS and polyketide libraries.

With respect to item (1) above, preferred examples include construction of chimeric PKS enzymes wherein the erythromycin PKS and rapamycin PKS function as accepting scaffolds, and one or more of the above-identified epothilone domains are inserted as replacements for domains of comparable function. Of course, construction of such enzymes is most effectively achieved by construction of appropriate encoding polynucleotides. In this regard, the examples of erythromycin PKS and rapamycin PKS are expected to be preferred given the low sequence homology between Sorangium and Streptomyces DNA, which is useful to avoid undesireable recombination events. In this example of the invention, it is not necessary to replace an entire domain of the scaffold PKS with an entire domain of epothilone PKS, rather peptide subsequences of a PKS domain that correspond to a peptide subsequence in a scaffold domain, or which otherwise provide useful function, may be used as replacements. Accordingly, appropriate encoding DNAs for construction of such chimeric PKS include those that encode at least 10, preferably 15, and most preferably 20 or more amino acids of a selected epothilone domain.

Additional information concerning construction and expression of encoding DNAs for the novel PKS of the invention, and concerning combinatorial approaches, is as follows.

Broadly, the invention provides recombinant materials for the production of combinatorial libraries of polyketides wherein the polyketide members of the library are synthesized by PKS systems derived from naturally occurring PKS systems that are used as scaffolds. Generally, many members of these libraries may themselves be novel compounds and the invention further includes novel polyketide members of these libraries. The invention methods may be directed to the preparation of an individual polyketide. The polyketide may or may not be novel, but the method of preparation permits a more convenient method of preparing it. The resulting polyketides may be further modified to convert them to antibiotics, typically, through glycosylation.

In another aspect, the invention is directed to a multiplicity of cell colonies comprising a library of colonies wherein each colony of the library contains an expression vector for the production of a different modular PKS, but derived from a naturally occurring PKS. In a preferred embodiment, the different PKS are derived from the erythromycin PKS. In any case, the library of different modular PKS is obtained by modifying one or more of the regions of a naturally occurring gene or gene cluster encoding an enzymatic activity so as to alter that activity, leaving intact the scaffold portions of the naturally occurring gene. Preferably, the replacing activity is represented by a domain of epothilone PKS or a subset thereof. The invention is also directed to methods to produce libraries of PKS complexes and to produce libraries of polyketides by culturing these colonies, as well as to the libraries so produced. In addition, the invention is directed to methods to screen the resulting polyketide libraries and to novel polyketides contained therein.

Regardless of the naturally occurring PKS gene used as a scaffold, the invention provides libraries or individual modified forms, ultimately of polyketides, by generating modifications in the erythromycin PKS or other naturally occurring PKS gene cluster so that the protein complexes produced by the cluster have altered activities in one or more respects, and thus produce polyketides other than the natural product of the PKS. Novel polyketides may thus be prepared, or polyketides in general prepared more readily, using this method. By providing a large number of different genes or gene clusters derived from a naturally occurring PKS gene cluster, each of which has been modified in a different way from the native cluster, an effectively combinatorial library of polyketides can be produced as a result of the multiple variations in these activities. Again, use of epothilone PKS domains is preferred.

In summary, a polyketide synthase "derived from" a naturally occurring PKS contains the scaffolding encoded by all the portion employed of the naturally occurring synthase gene, contains at least two modules that are functional, and contains mutations, deletions, or replacements of one or more of the activities of these functional modules so that the nature of the resulting polyketide is altered. This definition applies both at the protein and genetic levels. Particular preferred embodiments include those wherein a KS, AT, KR, DH or ER has been deleted or replaced by a version of the activity from a different PKS or from another location within the same PKS. Also preferred are derivatives where at least one noncondensation cycle enzymatic activity (KR, DH or ER) has been deleted or wherein any of these activities has been mutated so as to change the ultimate polyketide synthesized.

Thus, there are five degrees of freedom for constructing a polyketide synthase in terms of the polyketide that will be produced. First, the polyketide chain length will be determined by the number of modules in the PKS. Second, the nature of the carbon skeleton of the PKS will be determined by the specificities of the acyl transferases which determine the nature of the extender units at each position—e.g., malonyl, methyl malonyl, or ethyl malonyl, etc. Third, the loading domain specificity will also have an effect on the resulting carbon skeleton of the polyketide. Thus, the loading domain may use a different starter unit, such as acetyl, propionyl, and the like. Fourth, the oxidation state at various positions of the polyketide will be determined by the dehydratase and reductase portions of the modules. This will determine the presence and location of ketone, alcohol, alkene or alkane substituents at particular locations in the polyketide. Finally, the stereochemistry of the resulting polyketide is a finction of three aspects of the synthase. The first aspect is related to the AT/KS specificity associated with substituted malonyls as extender units, which affects stereochemistry only when the reductive cycle is missing or when it contains only a ketoreductase since the dehydratase would abolish chirality. Second, the specificity of the ketoreductase will determine the chirality of any β-OH. Finally, the enoyl reductase specificity for substituted malonyls as extender units will influence the result when there is a complete KR/DH/ER available.

Methods useful in support of construction of novel modular PKS are as follows.

A large number of modular PKS gene clusters have been mapped and/or sequenced. including for erythromycin and rapamycin, which have been completely mapped and sequenced, and for soraphen A, FK506 and oleandomycin which have been partially sequenced, and for candicidin, avermectin, and nemadectin which have been mapped and partially sequenced. Additional modular PKS gene clusters are expected to be available as time progresses. These genes can be manipulated using standard techniques to delete or inactivate activity encoding regions, insert regions of genes encoding corresponding activities from the same or different PKS systems, or be otherwise mutated using standard procedures for obtaining genetic alterations. Of course, portions of, or all of, the desired derivative coding sequences can be synthesized using standard solid phase synthesis methods such as those described by Jaye et al., *J Biol Chem* (i 984) 259:6331 and which are available commercially fron for example, Applied Biosystems, Inc.

In order to obtain nucleotide sequences encoding a variety of derivatives of the naturally occurring PKS, and thus a variety of polyketides for construction of a library, a desired number (97of constructs can be obtained by "mixing and matching" enzymatic activity-encoding portions, and mutations can be introduced into the native host PKS gene cluster or portions thereof. Use of encoding sequence for epothilone domains is preferred.

Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion. (See, e.g. , Kunkel, T. A. *Proc Natl Acad Sci USA* (1985) 82:448; Geisselsoder et al. *Bio Techniques* (1987) 5:786.) Alternatively, the mutations can be effected using a mismatched primer (generally 10–20 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. Zoller and Smith, *Methods in Enzymology* (1983) 100:468. Primer extension, is effected using DNA polymerase. The product of the extension reaction was cloned and those clones containing the mutated DNA were selected. Selection can be accomplished using the mutant primer as a hybridization probe. The technique is also applicable for generating multiple point mutations. See, e.g., Dalbie-McFarland et al. *Proc Natl Acad Sci USA* (1982) 79:6409. PCR mutagenesis will also find use for effecting the desired mutations.

Random mutagenesis of selected portions of the nucleotide sequences encoding enzymatic activities can be accomplished by several different techniques known in the art, e.g., by inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants or by damaging plasmid DNA in vitro with chemicals. Chemical mutagens include, for example, sodium bisulfite, nitrous acid, hydroxylamine, agents which damage or remove bases thereby preventing normal base-pairing such as hydrazine or formic acid, analogues of nucleotide precursors such as nitrosoguanidine, 5-bromouracil, 2-aminopurine, or acridine intercalating agents such as proflavine, acriflavine, quinacrine, and the like. Generally, plasmid DNA or DNA fragments are treated with chemicals, in transformed into *E. coli* and propagated as a pool or library of mutant plasmids.

In addition to providing mutated forms of regions encoding enzymatic activity, regions encoding corresponding activities from different PKS synthases or from different locations in the same PKS synthase can be recovered, for example, using PCR techniques with appropriate primers. By "corresponding" activity encoding regions is meant those regions encoding the same general type of activity—e.g., a ketoreductase activity in one location of a gene cluster would "correspond" to a ketoreductase-encoding activity in another location in the gene cluster or in a different gene cluster; similarly, a complete reductase cycle could be considered corresponding—e.g., KR/DH/ER would correspond to KR alone.

If replacement of a particular target region in a host polyketide synthase is to be made, this replacement can be conducted in vitro using suitable restriction enzymes or can be effected in vivo using recombinant techniques involving homologous sequences framing the replacement gene in a donor plasmid and a receptor region in a recipient plasmid. Such systems, advantageously involving plasmids of differing temperature sensitivities are described for example, in PCT application WO 96/40968.

The vectors used to perform the various operations to replace the enzymatic activity in the host PKS genes or to support mutations in these regions of the host PKS genes may be chosen to contain control sequences operably linked to the resulting coding sequences in a manner that expression of the coding sequences may be effected in a appropriate host. However, simple cloning vectors may be used as well.

If the cloning vectors employed to obtain PKS genes encoding derived PKS lack control sequences for expression operably linked to the encoding nucleotide sequences, the nucleotide sequences are inserted into appropriate expression vectors. This need not be done individually, but a pool of isolated encoding nucleotide sequences can be inserted into host vectors, the resulting vectors transformed or transfected into host cells and the resulting cells plated out into individual colonies.

Suitable control sequences include those which function in eucaryotic and procaryotic host cells. Preferred hosts include fungal systems such as yeast and procaryotic hosts, but single cell cultures of, for example, mammalian cells could also be used. There is no particular advantage, however, in using such systems. Particularly preferred are yeast and procaryotic hosts which use control sequences compatible with Streptomyces spp. Suitable controls sequences for single cell cultures of various types of organisms are well known in the art. Control systems for expression in yeast, including controls which effect secretion are widely available and are routinely used. Control elements include promoters, optionally containing operator sequences, and other elements depending on the nature of the host, such as ribosome binding sites. Particularly useful promoters for procaryotic hosts include those from PKS gene clusters which result in the production of polyketides as secondary metabolites, including those from aromatic (Type II) PKS gene clusters. Examples are act promoters, tcm promoters, spiramycin promoters, and the like. However, other bacterial promoters, such as those derived from sugar metabolizing enzymes, such as galactose, lactose (lac) and maltose, are also useful. Additional examples include promoters derived from biosynthetic enzymes such as for tryptophan (trp), the β-lactamase (bla), bacteriophage lambda PL, and T5. In addition, synthetic promoters, such as the tac promoter (U.S. Pat. No. 4,551,433), can be used.

Other regulatory sequences may also be desirable which allow for regulation of expression of the PKS replacement sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes which confer antibiotic resistance or sensitivity to the plasmid. Alternatively, several polyketides are naturally colored and this characteristic provides a built-in marker for screening cells successfully transformed by the present constructs.

The various PKS nucleotide sequences, or a cocktail of such sequences, can be cloned into one or more recombinant vectors as individual cassettes, with separate control elements, or under the control of, e.g., a single promoter. The PKS subunits or cocktail components can include flanking restriction sites to allow for the easy deletion and insertion of other PKS subunits or cocktail components so that hybrid PKSs can be generated. The design of such unique restriction sites is known to those of skill in the art and can be accomplished using the techniques described above, such as site-directed mutagenesis and PCR As described above, particularly useful control sequences are those which themselves, or using suitable regulatory systems, activate expression during transition from growth to stationary phase in the vegetative mycelium. The system contained in the plasmid identified as pCK7, i.e., the actI/actIII promoter pair and the actII-ORF4 (an activator gene), is particularly preferred Particularly preferred hosts are those which lack their own means for producing polyketides so that a cleaner result is obtained. Illustrative host cells of this type include the modified *S. coelicolor* CH999 culture described in PCT application WO 96140968 and similar strains of *S. lividans*.

The expression vectors containing nucleotide sequences encoding a variety of PKS systems for the production of different polyketides are then transformed into the appropriate host cells to construct the library. In one straightforward approach, a mixture of such vectors is transformed into the selected host cells and the resulting cells plated into individual colonies and selected for successful transformants. Each individual colony will then represent a colony with the ability to produce a particular PKS synthase and ultimately a particular polyketide. Typically, there will be duplications in some of the colonies; the subset of the transformed colonies that contains a different PKS in each member colony can be considered the library. Alternatively, the expression vectors can be used individually to transform hosts, which transformed hosts are then assembled into a library. A variety of strategies might be devised to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, more preferably at least 50, reflecting similar numbers of different altered PKS gene clusters and PKS gene products. The number of members in the library is arbitrarily chosen; however, the degrees of freedom outlined above with respect to the variation of starter, extender units, stereochemistry, oxidation state, and chain length is quite large.

Methods for introducing the recombinant vectors of the present invention into suitable hosts are known to those of skill in the art and typically include the use of $CaCl_2$ or other agents, such as divalent cations, lipofection, DMSO, protoplast transformation and electroporation.

As disclosed in the co-pending application entitled "Production of Polyketides in Bacteria and Yeasts" (of Phillip J. Barr et al., identified as Express Mail Label No. EH 493640115US, as filed on Dec. 11, 1997) incorporated herein by reference, a wide variety of hosts can be used, even though some hosts natively do not contain the appropriate post-translational mechanisms to activate the acyl carrier proteins of the synthases. These hosts can be modified with the appropriate recombinant enzymes to effect these modifications.

The polyketide producing colonies can be identified and isolated using known techniques and the produced polyketides further characterized. The polyketides produced by these colonies can be used collectively in a panel to represent a library or may be assessed individually for activity.

The libraries can thus be considered at four levels: (1) a multiplicity of colonies each with a different PKS encoding sequence encoding a different PKS cluster but all derived from a naturally occurring PKS cluster; (2) colonies which contain the proteins that are members of the PKS produced by the coding sequences; (3) the polyketides produced; and (4) antibiotics derived from the polyketides. Of course, combination libraries can also be constructed wherein members of a library derived, for example, from the erythromycin PKS can be considered as a part of the same library as those derived from, for example, the rapamycin PKS cluster.

Colonies in the library are induced to produce the relevant synthases and thus to produce the relevant polyketides to obtain a library of candidate polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand. Binding can be detected either directly or through a competition assay. Means to screen such libraries for binding are well known in the art. Alternatively, individual polyketide members of the library can be tested against a desired target. In this event, screens wherein the biological response of the target is measured can more readily be included.

EXAMPLES

Example 1

Identification of a Nucleotide Sequence Encoding a Ketoreductase (KR) Domain of Epothilone Polyketide Synthase A culture of *Sorangium cellulosum* SMP44 was grown on agar plates using filter paper as carbon source. The cells were scraped from the plate, suspended in water, and collected by centrifugation. The cells were then resuspended in 1 ml of 25% sucrose, 1 mM EDTA, 0.5 M Tris-HCl, pH 7.8. A 450 µl aliquot of the suspension was mixed with 200 µl of 5% SDS, 125 mM EDTA, 0.5 M Tris-HCl, pH 7.6, and then treated with 3 µl of ribonuclease A (1 mg/ml).

After incubation of this mixture at 70° C. for 30 minutes, 100 µl of 5M potassium acetate was added, and the mixture was placed on ice for 15 minutes. Solids were removed by centrifugation, and the supernatant was extracted twice with equal volumes of phenol/chloroform. The genomic DNA was precipitated from the aqueous phase by addition of ethanol, and then redissolved in 10 mM Tris-HCl, 1 mM EDTA.

Primers derived from the published sequence of the soraphen polyketide synthase genes (see T. Schupp et al., *Journal of Bacteriology*, 177, pp. 3673–3679, 1995) were used to amplify ketoreductase sequences (KR) from the genomic DNA of SMP44.

The primers used were

```
                                        (SEQ ID NO: 15)
(forward): CGGATCCCAG GGCGTCGAGG AAGGCG (SEQ ID NO: 16)
(reverse): GGAATTCATC ACCGGAGGCA CCGGC
```

The resultant PCR fragment was subcloned using the EcoRI and BamHI sites introduced by the PCR primers. Sequencing of the plasmid DNA form one resultant clone gave:

```
                                        (SEQ ID NO: 17)
GGATCCCATG GCGTCGAGGA AGGCGTTGGC GGCGGCGTAA

TTGGACTGGG CGGGGCTCCC GAGCACCCCG GAGAGCGACG

AGAACAGGAC GAAGGCGCGC AGCGGGCTGT GGCGCGTCTG

CTCGTCGAGG TTGACGGCCG CGTCGACCTT GGCCCGGAGC

ACGGCGCTCA GGCGCGCCGG CGTCATCGAG GAGAGCACGC
```

-continued

```
CGTCGTCGAG TGTGCCTGCG GCGTGCACGA CGGCGGTCAG

CGGCCTGTCG TGCGGGATGG CGAGCAGCAC CCGCTCGAGG

GCGACGCGAT CGGCAGCGTC CGCGGCGGCG ACGACGACGG

AGGCGCCGCG CGCCTGGAGC TCCGCGGCGA GGTCGGATGC

GCCGGGAGCA TCCGGGCCCC GGCGCGAGAG CAGCACCAGG

TGCTTGACGC CGTGGCGGTC GACGAGGCGA CGCGCCACGA

GAGCGCCGAG GGTGCCGGTG CCTCCGGTGA TGAATTC
``` wherein nucleotide sequence corresponding to primers is underlined.

The resultant coding strand DNA,

```
                                          (SEQ ID NO:2)
gaattcatca ccggaggcac cggcaccctc ggcgctctcg tggcgcgtcg cctcgtcgac cgccacggcg tcaagcacct ggtgctgctc tcgcgccggg gcccggatgc tcccggcgca tccgacctcg ccgcggagct ccaggcgcgc ggcgcctccg tcgtcgtcgc cgccgcggac gctgccgatc gcgtcgccct cgagcgggtg ctgctcgcca tcccgcacga caggccgctg accgccgtcg tgcacgccgc aggcacactc gacgacggcg tgctctcctc gatgacgccg gcgcgcctga gcgccgtgct ccgggccaag gtcgacgcgg ccgtcaacct cgacgagcag acgcgccaca gcccgctgcg cgccttcgtc ctgttctcgt cgctctccgg ggtgctcggg agccccgccc agtccaatta cgccgccgcc aacgccttcc tcgacgccat gggatcc,
``` encodes amino acid sequence (SEQ ID NO:1) corresponding to a ketoreductase (KR) domain of epothilone polyketide synthase, as evidenced by its homology to known ketoreductase domain sequences. This is demonstrated by reference to FIG. 1, Panel A, which shows a comparison of known KR domain sequences from within certain PKS that produce soraphens (SEQ ID NOS: 18,19) and an erythromycin (SEQ ID NO: 20). Based on the structure of epothilone, all modules of the epothilone PKS, except No. 7, are expected to have KR domains. The module number to which SEQ ID NO: 1 corresponds has not yet been determined.

Example 2

Isolation and Structure of Cosmid pKos28-26

A general ketosynthase domain probe was generated from *Sorangium cellulosum* SMP44 chromosomal DNA using degenerate primers designed by alignment of ketosynthase (KS) domains from a number of polyketide synthases. The degenerate primers used were as follows, wherein bases are designated using art-recognized single letter designations as also provided for in 37 CFR 1.822(b)(1):

```
                                 (SEQ ID NO: 22)
primer 1: 5'-RTG SGC RTT VGT NCC RCT-3'
```

```
                                 (SEQ ID NO: 23)
primer 2; 5'-GAC ACV GCN TGY TCB TCV-3'
``` wherein R=A and G; Y=C and T; S=G and C; B=G and T and C; N=A and G and C and T; and V=G and A and C.

The resultant PCT product was approximately 800 bp long, and was then non-radioactively labelled with DIG nucleotides (Boehringer Mannheim) for detection. A cosmid library of partial Sau3A digested chromosomal DNA fragments from *Sorangium cellulosum* SMP44 was generated in the Supercos system (Stratagene). The library was then screened by colony hybridization using the general KS domain probe. Cosmid pKos28-26 was identified as a cosmid that hybridized with the KS domain probe. In one set of experiments, sequences A, B, C and D in the cosmid (see FIG. 2) were conveniently studied because of the placement of Nsi I and Hind III restriction sites. Following use of the restriction enzymes, two small fragments (containing the A and B, and also the C and D regions, see FIG. 2) were subcloned and sequenced. Nucleotide sequences for cosmid regions A, B, C and D are reported herein as SEQ ID NOS: 11, 12, 13 and 14 respectively, and the amino acids encoded thereby as SEQ ID NOS: 7, 8, 9 and 10 respectively.

In general, encoding DNA for polyketide synthase modules ranges from about 3 to 5 kb (depending on the reductive cycle activities that are present), and in general have one of the following domain orders:

KS-AT-DH-ER-KR-ACP

KS-AT-DH-KR-ACP

KS-AT-KR-ACP

KS-AT-ACP.

Examination of the epothilone structure, based on art-recognized understandings of polyketide synthase reactions, predicts the presence of 8 synthase modules in the PKS, encoded by up to about 40 kb of DNA. Based on recognized sequence homologies, it was determined that: Sequence A codes for a DH and a KR domain region; Sequence B codes for a KS domain region, and also a region linking the KS to an AT domain region; Sequence C codes for an AT domain that is malonyl-CoA specific; and Sequence D codes for a DH domain region.

Reference to the map of the pKos28-26 cosmid thus indicates that at least 3 modules are represented, with Sequence A being near the end of one module, Sequence B being toward the middle of the next module, and Sequences C and D both being near the middle of the third module.

Example 3

Sequence Homology in Ketosynthase Domains

Additional fragments of encoding sequence for ketosynthase domains (KS) of epothilone polyketide synthase have also been isolated, and the corresponding amino acid sequences determined. FIG. 1, panel B, presents a comparison of these fragments (for SEQ ID NOS: 4, 6, which encode amino acid sequences represented by SEQ ID NOS: 3 and 5 respectively) to an erythromycin module 1 ketosynthase domain fragment (DEBS KS1, SEQ ID NO:21). The common amino acid element Cys-Ser-Ser-Ser-Leu (FIG. 1B, susbset of SEQ ID NOS: 3and 5) is a recognized active site motif within a KS domain, and Gly-Thr-Asn-Ala-His (FIG. 1B, susbset of SEQ ID NOS: 3and 5) is a recognized element marking the C-terminal end of such a domain.

SEQUENCE LISTING

<160> NUMBER OF SEQ ID NOS: 23

<210> SEQ ID NO 1
<211> LENGTH: 159
<212> TYPE: PRT
<213> ORGANISM: Sorangium cellulosum

<400> SEQUENCE: 1

```
Glu Phe Ile Thr Gly Gly Thr Gly Thr Leu Gly Ala Leu Val Ala Arg
  1               5                  10                  15

Arg Leu Val Asp Arg His Gly Val Lys His Leu Val Leu Leu Ser Arg
             20                  25                  30

Arg Gly Pro Asp Ala Pro Gly Ala Ser Asp Leu Ala Ala Glu Leu Gln
         35                  40                  45

Ala Arg Gly Ala Ser Val Val Val Ala Ala Ala Asp Ala Ala Asp Arg
     50                  55                  60

Val Ala Leu Glu Arg Val Leu Leu Ala Ile Pro His Asp Arg Pro Leu
 65                  70                  75                  80

Thr Ala Val Val His Ala Ala Gly Thr Leu Asp Asp Gly Val Leu Ser
                 85                  90                  95

Ser Met Thr Pro Ala Arg Leu Ser Ala Val Leu Arg Ala Lys Val Asp
            100                 105                 110

Ala Ala Val Asn Leu Asp Glu Gln Thr Arg His Ser Pro Leu Arg Ala
        115                 120                 125

Phe Val Leu Phe Ser Ser Leu Ser Gly Val Leu Gly Ser Pro Ala Gln
    130                 135                 140

Ser Asn Tyr Ala Ala Ala Asn Ala Phe Leu Asp Ala Met Gly Ser
145                 150                 155
```

<210> SEQ ID NO 2
<211> LENGTH: 477
<212> TYPE: DNA
<213> ORGANISM: Sorangium cellulosum

<400> SEQUENCE: 2

```
gaattcatca ccggaggcac cggcaccctc ggcgctctcg tggcgcgtcg cctcgtcgac     60
cgccacggcg tcaagcacct ggtgctgctc tcgcgccggg gcccggatgc tcccggcgca    120
tccgacctcg ccgcggagct ccaggcgcgc ggcgcctccg tcgtcgtcgc cgccgcggac    180
gctgccgatc gcgtcgccct cgagcgggtg ctgctcgcca tcccgcacga caggccgctg    240
accgccgtcg tgcacgccgc aggcacactc gacgacggcg tgctctcctc gatgacgccg    300
gcgcgcctga gcgccgtgct ccgggccaag gtcgacgcgg ccgtcaacct cgacgagcag    360
acgcgccaca gcccgctgcg cgccttcgtc ctgttctcgt cgctctccgg ggtgctcggg    420
agccccgccc agtccaatta cgccgccgcc aacgccttcc tcgacgccat gggatcc       477
```

<210> SEQ ID NO 3
<211> LENGTH: 250
<212> TYPE: PRT
<213> ORGANISM: Sorangium cellulosum
<220> FEATURE:
<223> OTHER INFORMATION: Xaa at various positions throughout the
      sequence may be any, other or unknown amino acid

<400> SEQUENCE: 3

```
Asp Thr Ala Cys Ser Ser Ser Leu Val Ser Leu His Leu Ala Cys Thr
  1               5                  10                  15
```

Ala Leu Arg Gln Gly Glu Cys Asp Leu Ala Leu Thr Gly Gly Val Met
            20                  25                  30

Val Ile Thr Thr Pro Ala Gly Phe Val Xaa Phe Ser Arg Ala Arg Gly
        35                  40                  45

Leu Ala Arg Asp Gly Arg Cys Lys Ser Phe Ser Ala Gln Ala Asp Gly
    50                  55                  60

Val Ile Trp Ser Glu Gly Cys Gly Met Leu Leu Lys Arg Leu Ser
65                  70                  75                  80

Asp Ala Arg Arg Asp Arg Asp Arg Val Leu Gly Val Ile Arg Gly Ser
                85                  90                  95

Ala Val Asn Gln Asp Arg Arg Ser Gln Gly Leu Thr Ala Pro Asn Gly
            100                 105                 110

Pro Ala Gln Gln Arg Val Ile Arg Gln Ala Leu Ser Ser Cys Gly Leu
        115                 120                 125

Ser Pro Glu Asn Arg Arg Gly Gly Gly Ala Trp Asp Gly Thr Ser Leu
    130                 135                 140

Gly Asp Pro Ile Glu Ala Gly Ala Leu Ala Glu Val Phe Gly Pro Glu
145                 150                 155                 160

Arg Ser Pro Glu Arg Pro Leu Tyr Leu Gly Ser Ser Lys Ser Asn Leu
                165                 170                 175

Gly His Ala Gln Ala Ala Gly Val Ala Gly Val Ile Lys Met Val
            180                 185                 190

Leu Ala Leu Gln His Glu Val Leu Pro Lys Thr Leu His Ala Glu Gln
        195                 200                 205

Pro Ser Pro His Ile Ala Trp Glu Gly Ser Gly Leu Ser Leu Leu Gln
    210                 215                 220

Glu Ala Arg Pro Trp Arg Arg Asn Gly Arg Val Arg Arg Ala Gly Val
225                 230                 235                 240

Ser Ser Phe Gly Ile Ser Gly Thr Asn Ala
                245                 250

<210> SEQ ID NO 4
<211> LENGTH: 751
<212> TYPE: DNA
<213> ORGANISM: Sorangium cellulosum

<400> SEQUENCE: 4
gacacggctt gttcgtcgtc gctggtgtcg ctgcacctgg cgtgcacggc gctgcgccag      60
ggcgaatgcg acctggcgct gaccggcggg gtgatggtga tcaccacccc cgcgggattc     120
gtttagttca gtcgtgcccg ggggcttgcg cgagacggtc ggtgcaagag cttctctgcc     180
caggctgacg gcgtcatctg gtccgaaggg tgcgggatgc tgttgctgaa gcggctgtct     240
gacgcgcggc gcgaccgcga ccgtgtgctg ggggtgatcc gtggctctgc ggtgaaccag     300
gaccgtcgca gccagggtct gacggcgccg aacggccctg cccagcagcg ggtgatccgg     360
caggcgctgt cgtcgtgtgg tctgtcgccc gagaatcgac gcggtggagg cgcatgggac     420
ggtacgagcc tcggagaccc gatcgaggcc ggagcgctgg cggaggtgtt tggaccggag     480 cgtagcccg agcgtccgct gtacctgggg tcgtcgaagt cgaacctggg acatgcgcag     540
gcggccgcgg gtgtggcggg cgtgatcaag atggtgctgg cgctgcagca cgaggtgctg     600
ccgaagacgc tgcatgcgga gcagccgagc ccgcacatcg cgtgggaggg gagcgggctg     660
tcattgctgc aagaggcgcg tccgtggcgg cgcaacggcc gggtccgtcg tgccggcgtg     720
tcgtcgttcg ggatcagcgg aactaacgcc c                                   751

<210> SEQ ID NO 5
<211> LENGTH: 197
<212> TYPE: PRT
<213> ORGANISM: Sorangium cellulosum
<220> FEATURE:
<223> OTHER INFORMATION: Xaa at various positions throughout the
      sequence may be any, other or unknown amino acid

<400> SEQUENCE: 5

```
Phe Phe Gly Cys Gln Ala Glu Arg Ala Arg Ala Gly Pro Arg Val Ala
  1               5                  10                  15

Gly Met Leu Leu Leu Lys Ala Ala Val Xaa Arg Ala Ala Arg Arg Arg
             20                  25                  30

Pro Cys Ala Gly Val Ile Arg Gly Ser Ala Val Asn Gln Asn Val Ala
         35                  40                  45

Ala Arg Phe Xaa Trp Arg Arg Thr Ala Leu Pro Ser Ser Gly Xaa Ser
     50                  55                  60

Gly Arg Ala Leu Ser Ser Cys Gly Leu Ser Pro Glu Asp Ile Asp Ala
 65                  70                  75                  80

Val Glu Ala His Gly Thr Gly Thr Ser Leu Gly Asp Pro Ile Glu Ala
                 85                  90                  95

Gly Ala Leu Ala Glu Val Phe Gly Pro Glu Arg Ser Pro Glu Arg Pro
            100                 105                 110

Leu Tyr Leu Gly Ser Ser Lys Ser Asn Leu Gly His Ala Gln Ala Ala
        115                 120                 125

Ala Gly Val Ala Gly Val Ile Lys Met Val Leu Ser Met Gln His Glu
    130                 135                 140

Val Leu Pro Lys Thr Leu His Ala Glu Gln Pro Ser Pro His Ile Gly
145                 150                 155                 160

Trp Glu Gly Ser Gly Leu Ser Leu Leu Gln Glu Ala Arg Pro Trp Arg
                165                 170                 175

Arg Asn Gly Arg Val Arg Arg Ala Gly Val Ser Ser Phe Gly Ile Ser
            180                 185                 190

Gly Thr Asn Ala His
        195
```

<210> SEQ ID NO 6
<211> LENGTH: 591
<212> TYPE: DNA
<213> ORGANISM: Sorangium cellulosum

<400> SEQUENCE: 6

| | | | | | |
|---|---|---|---|---|---|
| ttcttcggtt | gccaggcgga | acgggcgcgg | gctgggccga | gggttgcggg | aatgctgttg | 60 |
| ttgaaagcgg | ctgtctgacg | cgcagcgcga | cggcgaccgt | gtgctggggt | gatccgtggc | 120 |
| tctgcggtga | accagaacgt | cgcagccagg | ttctgatggc | gccgaacggc | cctgcccagc | 180 |
| agcgggtgat | ccggcagggc | gctgtcgtcg | tgtggtctgt | cgcccgagga | catcgacgcg | 240 |
| gtggaggcgc | acgtacggg | cacgagcctt | ggagacccga | tcgaggccgg | agcgctggcg | 300 |
| gaggtgtttg | gaccggagcg | tagccccgag | cgtccgctgt | acctgggatc | gtcgaagtcg | 360 |
| aacctcggac | atgcgcaggc | ggcggcgggc | gtggcgggcg | tgatcaagat | ggtgctgtcg | 420 |
| atgcagcacg | aggtgctgcc | gaagacgctg | cacgcggagc | agccgagccc | gcacattggg | 480 |
| tgggaaggaa | gcgggctgtc | gctgctgcaa | gaggcgcgtc | cgtggcggcg | caacggccgg | 540 |
| gtccgtcgtg | ccggcgtgtc | gtcgttcggg | atcagcggaa | ctaacgcgca | c | 591 |

<210> SEQ ID NO 7
<211> LENGTH: 260
<212> TYPE: PRT
<213> ORGANISM: Sorangium cellulosum
<220> FEATURE:
<223> OTHER INFORMATION: Xaa at various positions throughout the
      sequence may be any, other or unknown amino acid

<400> SEQUENCE: 7

Ala Leu Arg Ala Trp Ile Glu Arg Gly Ala Pro Thr Pro Val Arg Val
 1               5                  10                  15

Val Ile Asp Thr Asn Ala Ala Ser Ser Pro Arg Ser Asp Val Ala Gly
                20                  25                  30

Ser Ser His Glu Ala Thr Arg Gln Ala Leu Ser Leu Leu Gln Ala Trp
            35                  40                  45

Leu Ser Glu Pro Arg Leu Asp Ala Val Xaa Leu Val Trp Val Thr Arg
        50                  55                  60

Gly Ala Val Ser Ala Ala Pro Asp Asp Ala Val Xaa Asp Leu Ala His
 65                  70                  75                  80

Gly Pro Leu Trp Gly Leu Ile Arg Thr Ala Arg Ser Glu His Pro Glu
                85                  90                  95

Arg Arg Leu Arg Leu Ile Asp Val Gly Thr Xaa Pro Val Asp Thr Gly
               100                 105                 110

Leu Leu Ala Xaa Ala Leu Ala Thr Ala Ala Glu Pro Glu Leu Ala Leu
            115                 120                 125

Pro Arg Gly Pro Xaa Trp Pro Pro Ala Gly Ser Xaa Xaa Pro His Arg
        130                 135                 140

Lys Thr His Pro Thr Pro Arg Leu Asp Leu Pro Ala Pro Xaa Cys Xaa
145                 150                 155                 160

Xaa Asn Leu Gly Arg Leu Gly Xaa Ala Xaa Asn Pro Ser Cys Ser Pro
                165                 170                 175

Xaa Arg Val Xaa Ala Pro Phe Ser Xaa Leu Pro Pro Gly Ala Xaa Ser
            180                 185                 190

Pro Arg Ala Pro Asn Phe Ser Ile Leu Gln Glu Xaa Ala Pro Lys Pro
        195                 200                 205

Phe Asn Val Ala Ser Ile Phe Asn Arg Lys Asn Ser Pro Xaa Cys Arg
        210                 215                 220

Ile Xaa Pro Ala Pro Leu Thr Val Leu Pro Arg Xaa Val Ser Xaa Gly
225                 230                 235                 240

Phe Gln Thr Lys Pro Thr Xaa Cys Leu Ala Lys Val Arg Ala Pro Leu
                245                 250                 255

Xaa Ile Thr Asn
            260

<210> SEQ ID NO 8
<211> LENGTH: 249
<212> TYPE: PRT
<213> ORGANISM: Sorangium cellulosum
<220> FEATURE:
<223> OTHER INFORMATION: Xaa at various positions throughout the
      sequence may be any, other or unknown amino acid

<400> SEQUENCE: 8

Thr Lys Leu Arg Pro Lys Pro Xaa Xaa Arg Val Thr Thr Gly Phe Phe
 1               5                  10                  15

Val Gly Phe Xaa Arg Lys Leu Xaa Gly Xaa Xaa Gln Glu Arg His Xaa
                20                  25                  30

-continued

```
Leu Glu Xaa Asp Xaa Ala Gly Arg Leu Gly Lys Xaa Ser Xaa Leu Xaa
            35                  40                  45

Lys Xaa Ser Asn Arg Glu Pro Trp Xaa Xaa Glu Val Asn Leu Gly Xaa
    50                  55                  60

Arg Lys Val Arg Ala Xaa Asn Arg Val Phe Lys Met Cys Cys Ser Met
65                  70                  75                  80

Gln His Glu Xaa Leu Pro Lys Thr Xaa Arg Ser Ser Xaa Ala Gly
                85                  90                  95

His Trp Trp Arg Glu Arg Ala Phe Val Ala Ala Arg Gly Ala Ser Val
                100                 105                 110

Ala Ala Gln Arg Pro Gly Ala Arg Gly Arg Val Val Arg Ile
                115                 120                 125

Ser Gly Thr Asn Ala His Val Ile Leu Glu Glu Ala Pro Val Glu Ala
    130                 135                 140

Ala Arg Glu Pro Val Glu Ala Val Arg Glu Pro Val Glu Ala Glu Gly
145                 150                 155                 160

Val Ala Ile Pro Leu Leu Leu Ser Gly Arg Asp Glu Ala Ser Val Ala
                165                 170                 175

Ala Gln Ala Gly Arg Trp Ala Lys Trp Leu Glu Glu His Gly Glu Val
                180                 185                 190

Gly Trp Ser Asp Val Val Arg Thr Ala Ala Leu His Arg Thr His Phe
    195                 200                 205

Glu Ser Arg Ala Ser Val Leu Ala Ala Ser Ala Ala Gly Ala Val Glu
    210                 215                 220

Gly Leu Arg Ala Leu Ser Ser Gly Arg Pro Asp Ala Ala Val Val Ser
225                 230                 235                 240

Gly Thr Ala Lys Arg Gly Gly Lys Leu
                245

<210> SEQ ID NO 9
<211> LENGTH: 222
<212> TYPE: PRT
<213> ORGANISM: Sorangium cellulosum
<220> FEATURE:
<223> OTHER INFORMATION: Xaa at various positions throughout the
      sequence may be any, other or unknown amino acid

<400> SEQUENCE: 9

Lys Leu Ala Val Leu Phe Thr Gly Gln Gly Ser Gln Arg Leu Gly Met
1               5                   10                  15

Gly Lys Arg Leu Tyr Glu Val Tyr Pro Val Phe Arg Ala Ala Phe Asp
                20                  25                  30

Glu Val Cys Glu Ala Leu Asp Ala His Leu Asp Arg Gly Leu Arg Xaa
                35                  40                  45

Val Val Phe Ala Ala Ala Gly Ser Glu Glu Xaa Ala Gln Leu Glu Arg
    50                  55                  60

Thr Glu Tyr Thr Gln Pro Gly Leu Phe Ala Leu Glu Val Ala Leu Tyr
65                  70                  75                  80

Arg Gln Trp Xaa Ser Trp Gly Leu Asn Pro Leu Arg Cys Trp Gly Thr
                85                  90                  95

Arg Xaa Glu Xaa Xaa Thr Leu Arg Thr Xaa Arg Val Xaa Xaa Xaa Leu
                100                 105                 110

Arg Thr Gln Xaa Thr Xaa Val Pro Pro Xaa Ser Ala Asp Gln Gly Phe
    115                 120                 125

Gln Xaa Arg Gly Thr Met Phe Pro Xaa Lys Pro Pro Asn Pro Lys Xaa
    130                 135                 140
```

```
Thr Gly Xaa Ser Lys Ser Gly Gln Gly His Xaa Leu Pro Gly Xaa Pro
145                 150                 155                 160

Pro Ser Thr Ser Asn Xaa Thr Asn Ala Phe Xaa Val Ala His Ala Glu
                165                 170                 175

Pro Gly Arg Pro Pro Leu Ser Phe Xaa Leu Pro Pro His Xaa Glu Xaa
            180                 185                 190

Lys Ile Glu Val Pro Ile Leu Pro Pro Leu Arg Val Pro Xaa Ala Pro
            195                 200                 205

Cys Lys Thr Asn Xaa Ile Val Asp Xaa Xaa Gly Pro Lys Asn
    210                 215                 220

<210> SEQ ID NO 10
<211> LENGTH: 264
<212> TYPE: PRT
<213> ORGANISM: Sorangium cellulosum
<220> FEATURE:
<223> OTHER INFORMATION: Xaa at various positions throughout the
      sequence may be any, other or unknown amino acid

<400> SEQUENCE: 10

Gly Lys Xaa Xaa Xaa Leu Val Lys Phe Ala Xaa Ile Phe Gly Asn Ala
  1               5                  10                  15

Gly Gly Asp Phe Val Gly Pro Asn Arg Gly Gly Cys Leu Val Xaa Xaa
            20                  25                  30

His Arg Thr Gly Arg Asn Xaa Xaa Gly Gln Xaa Glu Gly Val Xaa Arg
        35                  40                  45

Arg Thr Leu Pro Leu Pro Gly Val Asp Glu Leu Xaa Xaa Ala His Ser
    50                  55                  60

Xaa Xaa Gly Gly Xaa Asp Phe Ser Gly Phe Thr Arg Val Asp Glu Val
65                  70                  75                  80

Ile Arg Leu Arg Pro Ala Phe Gln Gly Leu Trp Ser Xaa Arg Xaa Xaa
                85                  90                  95

Thr Asp Phe Phe Arg Pro Gly Val Phe Ala Gln Arg Arg Asp Glu Gln
            100                 105                 110

Arg Arg Gly Leu Arg Val His Pro Ala Xaa Met Asn Xaa Ala Leu His
        115                 120                 125

Thr Met Phe Ala Ala Phe Ala Glu Val Ser Ala Pro Xaa Asp Val Leu
    130                 135                 140

Leu Xaa Phe Ser Cys Ser Xaa Val Ala Leu His Ala Thr Gly Ala Ser
145                 150                 155                 160

Glu Xaa Arg Val Arg Leu Glu Xaa Ala Gly Gly Arg Asp Ser Ala Gln
                165                 170                 175

Ala Ala Ala Ser Leu Arg Val Thr Asp Ala Ala Gly Gln Pro Val Val
            180                 185                 190

Ser Val Gly Ala Leu His Leu Arg Arg Ala Thr Ala Glu Gln Leu Arg
        195                 200                 205

Ala Ala Thr His Ala Glu Ala Gln His Leu Tyr Arg Val Asp Phe Gln
    210                 215                 220

Leu Val Ser Leu Val Glu Ala Gly Ser Lys Val Asp Ser Leu Val Val
225                 230                 235                 240

Leu Arg Ala Pro Glu Gly Arg Gly Arg Leu Gly Glu Ala Leu Gly Val
                245                 250                 255

Glu Ala Ile Ala Gly Leu Asp Ala
            260
```

-continued

<210> SEQ ID NO 11
<211> LENGTH: 787
<212> TYPE: DNA
<213> ORGANISM: Sorangium cellulosum
<220> FEATURE:
<223> OTHER INFORMATION: "n" at various positions throughout the
      sequence may be A, T, C, G, other or unknown

<400> SEQUENCE: 11

| | | | | | |
|---|---|---|---|---|---|
| atgcattgcg | cgcttggatc | gagcggggcg | cgccaacgcc | tgtgcgggtg | gtgatcgaca | 60 |
| cgaacgctgc | cagctcaccg | cgctcggacg | tggcggggtc | gtcgcacgag | gcgacgaggc | 120 |
| aggcgctgtc | gctgctgcaa | gcgtggttgt | cggagccgcg | gctcgacgct | gtcganctgg | 180 |
| tgtgggtgac | gcggggcgcg | gtcagcgcag | ctccggacga | cgccgtcgan | gacctggcgc | 240 |
| acgggccgct | gtgggggctt | attcgcacgg | cgcgcagcga | gcaccccgag | cgccggctgc | 300 |
| gcttgatcga | tgtggggacc | gancccgtgg | acactgggct | gctggcgcng | cgctggcga | 360 |
| cggcggcgga | accngaactt | gccctgcccc | ggggcccgtn | ctggcccccc | gctggttccn | 420 |
| tacngccgca | ccgaaaaact | cacccaaccc | cccggctgga | ccttccggca | cctncttgtt | 480 |
| nacngaacct | tggccgtctt | gggcnagcgt | naaacccntc | ttgttccccc | ncngggtttt | 540 |
| aagcacctttt | ttctnaactt | cccccgggg | cctgaagccc | ccgggccccc | aactttcaa | 600 |
| tcctccaaga | aancgcccca | aaaccttttca | atgttgcttc | aattttcaac | cggaaaaatt | 660 |
| ccccttntg | ccggattaan | ccggcccccc | taaccgttct | nccccgctng | gtttcaaang | 720 |
| gttttcaaac | naagccaacc | ncttgtttgg | ccaaggtaag | ggcnccctc | cnaataacga | 780 |
| acgnttn | | | | | | 787 |

<210> SEQ ID NO 12
<211> LENGTH: 750
<212> TYPE: DNA
<213> ORGANISM: Sorangium cellulosum
<220> FEATURE:
<223> OTHER INFORMATION: "n" at various positions throughout the
      sequence may be A, T, C, G, other or unknown

<400> SEQUENCE: 12

| | | | | | |
|---|---|---|---|---|---|
| tgnaccaagc | taaggccgaa | gcccngcann | agggtaacna | caggctttt | tgtnggtttt | 60 |
| ncccgaaaat | taangggngn | ggnncaggaa | cggcacnccc | tngaantcga | ttgagccgga | 120 |
| cgnttgggga | agntttcggn | cttggncaag | cngagcaacc | gtgaaccttg | gttnntggaa | 180 |
| gtgaaccttg | gcangcgcaa | ggttcgggcg | gntaaccggg | tgttcaagat | gtgctgttcg | 240 |
| atgcagcacg | agntgctgcc | gaagacgtgn | aggcggagca | gcgagccgg | ncattggtgg | 300 |
| agggagcggg | ctttcgttgc | tgcaagaggc | gcgtccgtgg | cggcgcaacg | gccgggcgcg | 360 |
| gcgcgcgggc | gtgtcgtcgt | tcggatcagc | gggacgaacg | cccatgtcat | cctcgaagag | 420 |
| gcgccggtgg | aggcggctcg | cgagccggtg | gaggcggtgc | gcgagccggt | ggaggcggag | 480 |
| ggtgttgcga | taccgctgtt | gctgtcgggg | cgagacgagg | cctcggtggc | ggcgcaggcg | 540 |
| gggcggtggg | cgaagtggct | ggaagagcac | ggggaggtgg | ggtggtcgga | cgtggtgagg | 600 |
| acggcggcgc | tgcaccggac | gcacttcgag | tcgcgggcgt | cggtgcttgc | ggcgagcgct | 660 |
| gcgggagctg | tggagggtct | tcgcgcgctg | tcgtcggggc | ggccggatgc | ggcggtggtg | 720 |
| agcgggacgg | cgaagcgagg | cgggaagctt | | | | 750 |

<210> SEQ ID NO 13
<211> LENGTH: 667
<212> TYPE: DNA

-continued

<213> ORGANISM: Sorangium cellulosum
<220> FEATURE:
<223> OTHER INFORMATION: "n" at various positions throughout the
      sequence may be A, T, C, G, other or unknown

<400> SEQUENCE: 13

| | | | | | |
|---|---|---|---|---|---|
| aagcttgcgg | tgctgttcac | ggggcagggc | agccagcggc | tcgggatggg | gaagaggctt | 60 |
| tacgaagtgt | accccgtgtt | ccgtgcggcg | ttcgacgagg | tgtgcgaggc | gctggacgcg | 120 |
| catctcgacc | gtgggttgag | agangtggtg | ttcgcggccg | cgggcagcga | ggaangagcg | 180 |
| cagctggagc | ggacggagta | cacgcagccc | gggctgtttg | cgctggaagt | ggcgctgtac | 240 |
| cgtcagtggg | antcgtgggg | gctgaacccg | ctgcgctgct | ggggcactcg | atangaaanc | 300 |
| tgaacgctgc | gcacgtngcg | ggtntnctga | nccttgcgga | cgcagcnaac | tantgtnccc | 360 |
| ccgcngtcng | ctgatcaagg | gttccaagnc | cgggaaacca | tgtttccgtn | gaagcctccg | 420 |
| aacccgaagt | ncaccggcnc | ttcgaagtcn | ggccagggcc | acnaactccc | cggctaaccc | 480 |
| ccatccacgt | ctaacnggac | aaacgcgttc | nccgttgccc | acgctgagcc | cggccgcccc | 540 |
| ccgctttctt | ttncccttcc | accccatnac | gaacngaaaa | tcgaagtccc | gattcttccc | 600 |
| cccctgcgtg | taccntangc | accctgcaaa | accaattnca | ttgttgattn | caanggcccc | 660 |
| aagaacc | | | | | | 667 |

<210> SEQ ID NO 14
<211> LENGTH: 794
<212> TYPE: DNA
<213> ORGANISM: Sorangium cellulosum
<220> FEATURE:
<223> OTHER INFORMATION: "n" at various positions throughout the
      sequence may be A, T, C, G, other or unknown

<400> SEQUENCE: 14

| | | | | | |
|---|---|---|---|---|---|
| nggcaagngc | ngggntttgg | ttaaattcgc | ccntatttc | ggaaatgccg | ggggtgattt | 60 |
| tgttgggccc | aaccggggng | ggtgtttggt | tnaanaccac | cgnacaggac | ggaatncccn | 120 |
| tggtcaanag | gaagggggttt | nacgaagaac | cttgccactt | ccgggagttg | atgagctaan | 180 |
| anttgcccat | tccnggcncg | gaggcgntga | cttttcgggt | tttacgaggg | ttgatgaggt | 240 |
| gattcggtta | cgcccggcct | tccagggttt | gtggagctnt | cgnntcgana | cggactttt | 300 |
| tcgcccgggt | gtttttgccc | aaagacggga | cgaacagcgc | cgaggattac | gggtgcatcc | 360 |
| ggcgntgatg | aacnccgcgt | tgcatacgat | gttcgcagcg | tttgcggagg | tatcagcgcc | 420 |
| ggangacgtg | ctgctgcntt | tttcgtgttc | ggangtggcg | ttgcacgcca | cgggggcgag | 480 |
| cgagntccgg | gtgaggctgg | agntcgcagg | aggcagagac | tcggcacagg | cagccgcntc | 540 |
| gctgcgcgtt | acagatgccg | ccggccagcc | ggtggtgagc | gtcggtgccc | tgcatctgcg | 600 |
| ccgggcgacg | gccgagcagc | tgcgggcagc | gacgcatgcc | gaggcgcagc | acctgtaccg | 660 |
| ggtggacttc | cagctcgtga | gcctcgtgga | ggcgggctcg | aaggtggact | cgctggtggt | 720 |
| gctccgtgcg | cctgaggggc | gagggcgact | gggcgaagcg | ctgggtgtgg | aggcgatcgc | 780 |
| aggcctcgat | gcat | | | | | 794 |

<210> SEQ ID NO 15
<211> LENGTH: 26
<212> TYPE: DNA
<213> ORGANISM: Sorangium cellulosum

<400> SEQUENCE: 15
cggatcccag ggcgtcgagg aaggcg        26

<210> SEQ ID NO 16
<211> LENGTH: 25
<212> TYPE: DNA
<213> ORGANISM: Sorangium cellulosum

<400> SEQUENCE: 16
ggaattcatc accggaggca ccggc                                        25

<210> SEQ ID NO 17
<211> LENGTH: 477
<212> TYPE: DNA
<213> ORGANISM: Sorangium cellulosum

<400> SEQUENCE: 17
ggatcccatg gcgtcgagga aggcgttggc ggcggcgtaa ttggactggg cggggctccc    60
gagcaccccg gagagcgacg agaacaggac gaaggcgcgc agcgggctgt ggcgcgtctg   120
ctcgtcgagg ttgacggccg cgtcgacctt ggcccggagc acggcgctca ggcgcgccgg   180
cgtcatcgag gagagcacgc cgtcgtcgag tgtgcctgcg gcgtgcacga cggcggtcag   240
cggcctgtcg tgcgggatgg cgagcagcac ccgctcgagg gcgacgcgat cggcagcgtc   300
cgcggcggcg acgacgacgg aggcgccgcg cgcctggagc tccgcggcga ggtcggatgc   360
gccgggagca tccgggcccc ggcgcgagag cagcaccagg tgcttgacgc cgtggcggtc   420
gacgaggcga cgcgccacga gagcgccgag ggtgccggtg cctccggtga tgaattc     477

<210> SEQ ID NO 18
<211> LENGTH: 158
<212> TYPE: PRT
<213> ORGANISM: Sorangium cellulosum

<400> SEQUENCE: 18

Leu Leu Ile Thr Gly Gly Thr Gly Ala Ala Gly Ala His Val Ala Arg
  1               5                  10                  15

Trp Leu Ala Arg Glu Gly Ala Glu His Leu Val Leu Ile Ser Arg Arg
             20                  25                  30

Gly Ala Gln Ala Glu Gly Ala Ser Glu Leu His Ala Glu Leu Thr Ala
         35                  40                  45

Leu Gly Ala Arg Val Thr Phe Ala Ala Cys Asp Val Ala Asp Arg Ser
     50                  55                  60

Ala Val Ala Thr Leu Leu Glu Gln Leu Asp Ala Glu Gly Ser Gln Val
 65                  70                  75                  80

Arg Ala Val Phe His Ala Gly Ile Gly Arg His Ala Pro Leu Ala
                 85                  90                  95

Ala Thr Ser Leu Met Glu Leu Ala Asp Val Val Ser Ala Lys Val Leu
                100                 105                 110

Gly Ala Gly Asn Leu His Asp Leu Leu Gly Pro Arg Pro Leu Asp Ala
            115                 120                 125

Phe Val Leu Phe Ser Ser Ile Ala Gly Val Trp Gly Gly Gln Gln
        130                 135                 140

Ala Gly Tyr Ala Ala Gly Asn Ala Phe Leu Asp Ala Leu Ala
145                 150                 155

<210> SEQ ID NO 19
<211> LENGTH: 158
<212> TYPE: PRT
<213> ORGANISM: Sorangium cellulosum

```
<400> SEQUENCE: 19

Val Leu Ile Thr Gly Gly Thr Gly Thr Leu Gly Ala Leu Val Ala Arg
  1               5                  10                  15

Arg Leu Val Val Asn His Asp Ala Lys His Leu Leu Leu Thr Ser Arg
                 20                  25                  30

Gln Gly Ala Ser Ala Pro Gly Ala Asp Val Leu Arg Ser Glu Leu Glu
             35                  40                  45

Ala Leu Gly Ala Ser Val Thr Leu Ala Ala Cys Asp Val Ala Asp Pro
         50                  55                  60

Arg Ala Leu Lys Asp Leu Leu Asp Asn Ile Pro Ser Ala His Pro Val
 65                  70                  75                  80

Ala Ala Val Val His Ala Ala Ser Val Leu Asp Gly Asp Leu Leu Gly
                 85                  90                  95

Ala Met Ser Leu Glu Arg Ile Asp Arg Val Phe Ala Pro Lys Ile Asp
             100                 105                 110

Ala Ala Trp His Leu His Gln Leu Thr Gln Asp Lys Pro Leu Ala Ala
         115                 120                 125

Phe Ile Leu Phe Ser Ser Val Ala Gly Val Leu Gly Ser Ser Gly His
130                 135                 140

Ser Asn Tyr Ala Ala Ala Ser Ala Phe Leu Asp Ala Leu Ala
145                 150                 155

<210> SEQ ID NO 20
<211> LENGTH: 158
<212> TYPE: PRT
<213> ORGANISM: Sorangium cellulosum

<400> SEQUENCE: 20

Val Leu Val Thr Gly Gly Thr Gly Val Gly Gly Gln Ile Ala Arg
  1               5                  10                  15

Trp Leu Ala Arg Arg Gly Ala Pro His Leu Leu Val Ser Arg Ser
                 20                  25                  30

Gly Pro Asp Ala Asp Gly Ala Gly Glu Leu Val Ala Glu Leu Glu Ala
             35                  40                  45

Leu Gly Ala Arg Thr Thr Val Ala Ala Cys Asp Val Thr Asp Arg Glu
         50                  55                  60

Ser Val Arg Glu Leu Leu Gly Gly Ile Gly Asp Asp Val Pro Leu Ser
 65                  70                  75                  80

Ala Val Phe His Ala Ala Ala Thr Leu Asp Asp Gly Thr Val Asp Thr
                 85                  90                  95

Leu Thr Gly Glu Arg Ile Glu Arg Ala Ser Arg Ala Lys Val Leu Gly
             100                 105                 110

Ala Arg Asn Leu His Glu Leu Thr Arg Glu Leu Asp Leu Thr Ala Phe
         115                 120                 125

Val Leu Phe Ser Ser Phe Ala Ser Ala Phe Gly Ala Pro Gly Leu Gly
130                 135                 140

Gly Tyr Ala Pro Gly Asx Ala Tyr Leu Asp Gly Leu Ala Gln
145                 150                 155
```

```
<210> SEQ ID NO 21
<211> LENGTH: 249
<212> TYPE: PRT
<213> ORGANISM: Sorangium cellulosum

<400> SEQUENCE: 21
```

| Asp | Thr | Ala | Cys | Ser | Ser | Leu | Val | Ala | Val | His | Leu | Ala | Cys | Gln |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Ser Leu Arg Arg Gly Glu Ser Ser Leu Ala Met Ala Gly Gly Val Thr
            20                  25                  30

Val Met Pro Thr Pro Gly Met Leu Val Asp Phe Ser Arg Met Asn Ser
        35                  40                  45

Leu Ala Pro Asp Gly Arg Cys Lys Ala Phe Ser Ala Gly Ala Asn Gly
    50                  55                  60

Phe Gly Met Ala Glu Gly Ala Gly Met Leu Leu Leu Glu Arg Leu Ser
65              70                  75                  80

Asp Ala Arg Arg Asn Gly Pro Val Leu Ala Val Leu Arg Gly Thr Ala
                85                  90                  95

Val Asn Ser Asp Gly Ala Ser Asn Gly Leu Ser Ala Pro Asn Gly Arg
            100                 105                 110

Ala Gln Val Arg Val Ile Gln Gln Ala Leu Ala Glu Ser Gly Leu Gly
        115                 120                 125

Pro Ala Asp Ile Asp Ala Val Glu Ala His Gly Thr Gly Thr Arg Leu
    130                 135                 140

Gly Asp Pro Ile Glu Ala Arg Ala Leu Phe Glu Ala Tyr Gly Arg Asp
145                 150                 155                 160

Arg Glu Gln Pro Leu His Leu Gly Ser Val Lys Ser Asn Leu Gly His
                165                 170                 175

Thr Gln Ala Ala Ala Gly Val Ala Gly Val Ile Lys Met Val Leu Ala
            180                 185                 190

Met Arg Ala Gly Thr Leu Pro Arg Thr Leu His Ala Ser Glu Arg Ser
        195                 200                 205

Lys Glu Ile Asp Trp Ser Ser Gly Ala Ile Ser Leu Leu Asp Glu Pro
    210                 215                 220

Glu Pro Trp Pro Ala Gly Ala Arg Pro Arg Arg Ala Gly Val Ser Ser
225                 230                 235                 240

Phe Gly Ile Ser Gly Thr Asn Ala His
                245

```
<210> SEQ ID NO 22
<211> LENGTH: 18
<212> TYPE: DNA
<213> ORGANISM: Sorangium cellulosum
<220> FEATURE:
<223> OTHER INFORMATION: "n" at position 13 may be A, T, C or G

<400> SEQUENCE: 22
rtgsgcrttv gtnccrct                                                   18

<210> SEQ ID NO 23
<211> LENGTH: 18
<212> TYPE: DNA
<213> ORGANISM: Sorangium cellulosum
<220> FEATURE:
<223> OTHER INFORMATION: "n" at position 9 may be A, T, C or G

<400> SEQUENCE: 23
gacacvgcnt gytcbtcv                                                   18
```

We claim:

1. A polyketide synthase comprising a ketoreductase domain wherein said ketoreductase domain comprises a peptide sequence selected from the group consisting of:

(a) Val-Asp-Arg-His-Gly-Val-Lys-His-Leu-Val; (subset of SEQ ID NO:1)

(b) Gly-Ala-Ser-Asp-Leu-Ala-Ala-Glu-Leu-Gln; (subset of SEQ ID NO:1)

(c) Ala-Arg-Gly-Ala-Ser-Val-Val-Val-Ala-Ala; (subset of SEQ ID NO:1)

(d) Ala-Asp-Ala-Ala-Asp-Arg-Val-Ala-Leu-Glu; (subset of SEQ ID NO:1)

(e) Arg-Val-Leu-Leu-Ala-Ile-Pro-His-Asp-Arg; (subset of SEQ ID NO:1)

(f) Pro-Leu-Thr-Ala-Val-Val-His-Ala-Ala-Gly; (subset of SEQ ID NO:1)

(g) Thr-Leu-Asp-Asp-Gly-Val-Leu-Ser-Ser-Met; (subset of SEQ ID NO:1)

(h) Ala-Lys-Val-Asp-Ala-Ala-Val-Asn-Leu-Asp; (subset of SEQ ID NO:1)

(i) Glu-Gln-Thr-Arg-His-Ser-Pro-Leu-Arg-Ala; (subset of SEQ ID NO:1)

(j) Phe-Val-Leu-Phe-Ser-Ser-Leu-Ser-Gly-Val; (subset of SEQ ID NO:1)

and (k) Leu-Gly-Ser Pro Ala-Gln-Ser-Asn-Tyr-Ala Ala-Ala. (subset of SEQ ID NO:1)

2. The polyketide synthase defined in claim 1, wherein said ketoreductase domain includes the peptide sequence:

```
                                     (SEQ ID NO:1)
Thr-Leu-Gly-Ala-Leu-Val-Ala-Arg-Arg-Leu-
Val-Asp-Arg-His-Gly-Val-Lys-His-Leu-Val-
Leu-Leu-Ser-Arg-Arg-Gly-Pro-Asp-Ala-Pro-
Gly-Ala-Ser-Asp-Leu-Ala-Ala-Glu-Leu-Gln-
Ala-Arg-Gly-Ala-Ser-Val-Val-Val-Ala-Ala-
Ala-Asp-Ala-Ala-Asp-Arg-Val-Ala-Leu-Glu-
Arg-Val-Leu-Leu-Ala-Ile-Pro-His-Asp-Arg-
Pro-Leu-Thr-Ala-Val-Val-His-Ala-Ala-Gly-
Thr-Leu-Asp-Asp-Gly-Val-Leu-Ser-Ser-Met-
Thr-Pro-Ala-Arg-Leu-Ser-Ala-Val-Leu-Arg-
Ala-Lys-Val-Asp-Ala-Ala-Val-Asn-Leu-Asp-
Glu-Gln-Thr-Arg-His-Ser-Pro-Leu-Arg-Ala-
Phe-Val-Leu-Phe-Ser-Ser-Leu-Ser-Gly-Val-
Leu-Gly-Ser-Pro-Ala-Gln-Ser-Asn-Tyr-Ala-
Ala-Ala-,.
```

3. A purified and isolated DNA molecule that comprises an open reading frame of a polyketide synthase, wherein said open reading frame includes an encoding sequence for a ketoreductase domain that comprises:

```
                                              (SEQ ID NO:2)
gaattcatca ccggaggcac cggcaccctc ggcgctctcg
tggcgcgtcg cctcgtcgac cgccacggcg tcaagcacct
ggtgctgctc tcgcgccggg gcccggatgc tcccggcgca
tccgacctcg ccgcggagct ccaggcgcgc ggcgcctccg
tcgtcgtcgc cgccgcggac gctgccgatc gcgtcgccct
cgagcgggtg ctgctcgcca tcccgcacga caggccgctg
accgccgtcg tgcacgccgc aggcacactc gacgacggcg
tgctctcctc gatgacgccg gcgcgcctga gcgccgtgct
ccgggccaag gtcgacgcgg ccgtcaacct cgacgagcag
acgcgccaca gcccgctgcg cgccttcgtc ctgttctcgt
cgctctccgg ggtgctcggg agccccgccc agtccaatta
cgccgccgcc aacgccttcc tcgacgccat gggatcc,
``` or a continuous subset thereof that encodes at least 10 amino acids.

4. A polyketide synthase comprising a ketosynthase domain wherein said ketosynthase domain comprises a peptide sequence selected from the group consisting of:

(a) Leu-His-Leu-Ala-Cys-Thr-Ala-Leu-Arg-Gln-   (subset of SEQ ID NO:3);

(b) Gly-Glu-Cys-Asp-Leu-Ala-Leu-Thr-Gly-Gly-   (subset of SEQ ID NO:3);

(c) Val-Met-Val-Ile-Thr-Thr-Pro-Ala-Gly-Phe-   (subset of SEQ ID NO:3);

(d) Val-Xaa-Phe-Ser-Arg-Ala-Arg-Gly-Leu-Ala-   (subset of SEQ ID NO:3);

(e) Arg-Asp-Gly-Arg-Cys-Lys-Ser-Phe-Ser-Ala-   (subset of SEQ ID NO:3);

(f) Gln-Ala-Asp-Gly-Val-Ile-Trp-Ser-Glu-Gly-   (subset of SEQ ID NO:3);

-continued (g) Cys-Gly-Met-Leu-Leu-Leu-Lys-Arg-Leu-Ser-   (subset of SEQ ID NO:3);

(h) Asp-Ala-Arg-Arg-Asp-Arg-Asp-Arg-Val-Leu-   (subset of SEQ ID NO:3);

(i) Gly-Val-Ile-Arg-Gly-Ser-Ala-Val-Asn-Gln-   (subset of SEQ ID NO:3);

(j) Asp-Arg-Arg-Ser-Gln-Gly-Leu-Thr-Ala-Pro-   (subset of SEQ ID NO:3);

(k) Gln-Ala-Leu-Ser-Ser-Cys-Gly-Leu-Ser-Pro-   (subset of SEQ ID NO:3);

(l) Glu-Asn-Arg-Arg-Gly-Gly-Gly-Ala-Trp-Asp-   (subset of SEQ ID NO:3);

(m) Gly-Ala-Leu-Ala-Glu-Val-Phe-Gly-Pro-Glu-   (subset of SEQ ID NO:3);

(n) Arg-Ser-Pro-Glu-Arg-Pro-Leu-Tyr-Leu-Gly-   (subset of SEQ ID NO:3);

(o) Ser-Ser-Lys-Ser-Asn-Leu-Gly-His-Ala-Gln-   (subset of SEQ ID NO:3);

(p) Met-Val-Leu-Ala-Leu-Gln-His-Glu-Val-Leu-   (subset of SEQ ID NO:3);

(q) Pro-Lys-Thr-Leu-His-Ala-Glu-Gln-Pro-Ser-   (subset of SEQ ID NO:3);

(r) Pro-His-Ile-Ala-Trp-Glu-Gly-Ser-Gly-Leu-   (subset of SEQ ID NO:3);

and (s) Ser-Leu-Leu-Gln-Glu-Ala-Arg-Pro-Trp-Arg-   (subset of SEQ ID NO:3).

5. The polyketide synthase defined in claim 4 wherein said ketosynthase domain includes the peptide sequence:

```
                                     (SEQ ID NO:3)
Asp-Thr-Ala-Cys-Ser-Ser-Ser-Leu-Val-Ser-
Leu-His-Leu-Ala-Cys-Thr-Ala-Leu-Arg-Gln-
Gly-Glu-Cys-Asp-Leu-Ala-Leu-Thr-Gly-Gly-
Val-Met-Val-Ile-Thr-Thr-Pro-Ala-Gly-Phe-
Val-Xaa-Phe-Ser-Arg-Ala-Arg-Gly-Leu-Ala-
Arg-Asp-Gly-Arg-Cys-Lys-Ser-Phe-Ser-Ala-
Gln-Ala-Asp-Gly-Val-Ile-Trp-Ser-Glu-Gly-
Cys-Gly-Met-Leu-Leu-Leu-Lys-Arg-Leu-Ser-
Asp-Ala-Arg-Arg-Asp-Arg-Asp-Arg-Val-Leu-
Gly-Val-Ile-Arg-Gly-Ser-Ala-Val-Asn-Gln-
Asp-Arg-Arg-Ser-Gln-Gly-Leu-Thr-Ala-Pro-
Asn-Gly-Pro-Ala-Gln-Gln-Arg-Val-Ile-Arg-
Gln-Ala-Leu-Ser-Ser-Cys-Gly-Leu-Ser-Pro-
Glu-Asn-Arg-Arg-Gly-Gly-Gly-Ala-Trp-Asp-
Gly-Thr-Ser-Leu-Gly-Asp-Pro-Ile-Glu-Ala-
Gly-Ala-Leu-Ala-Glu-Val-Phe-Gly-Pro-Glu-
Arg-Ser-Pro-Glu-Arg-Pro-Leu-Tyr-Leu-Gly-
Ser-Ser-Lys-Ser-Asn-Leu-Gly-His-Ala-Gln-
Ala-Ala-Ala-Gly-Val-Ala-Gly-Val-Ile-Lys-
Met-Val-Leu-Ala-Leu-Gln-His-Glu-Val-Leu-
Pro-Lys-Thr-Leu-His-Ala-Glu-Gln-Pro-Ser-
Pro-His-Ile-Ala-Trp-Glu-Gly-Ser-Gly-Leu-
Ser-Leu-Leu-Gln-Glu-Ala-Arg-Pro-Trp-Arg-
Arg-Asn-Gly-Arg-Val-Arg-Arg-Ala-Gly-Val-
Ser-Ser-Phe-Gly-Ile-Ser-Gly-Thr-Asn-Ala-.
```

6. A purified and isolated DNA molecule that comprises an open reading frame of a polyketide synthase, wherein said open reading frame includes an encoding sequence for a ketosynthase domain that comprises:

```
GAC ACG GCT TGT TCG TCG TCG CTG GTG TCG CTG
CAC CTG GCG TGC ACG GCG CTG CGC CAG GGC GAA
TGC GAC CTG GCG CTG ACC GGC GGG GTG ATG GTG
ATC ACC ACC CCC GCG GGA TTC GTT TAG TTC AGT
CGT GCC CGG GGG CTT GCG CGA GAC GGT CGG TGC
AAG AGC TTC TCT GCC CAG GCT GAC GGC GTC ATC
TGG TCC GAA GGG TGC GGG ATG CTG TTG CTG AAG
CGG CTG TCT GAC GCG CGG CGC GAC CGC GAC CGT
GTG CTG GGG GTG ATC CGT GGC TCT GCG GTG AAC
CAG GAC CGT CGC AGC CAG GGT CTG ACG GCG CCG
AAC GGC CCT GCC CAG CAG CGG GTG ATC CGG CAG
GCG CTG TCG TCG TGT GGT CTG TCG CCC GAG AAT
CGA CGC GGT GGA GGC GCA TGG GAC GGT ACG AGC
CTC GGA GAC CCG ATC GAG GCC GGA GCG CTG GCG
GAG GTG TTT GGA CCG GAG CGT AGC CCC GAG CGT
CCG CTG TAC CTG GGG TCG TCG AAG TCG AAC CTG
GGA CAT GCG CAG GCG GCC GCG GGT GTG GCG GGC
GTG ATC AAG ATG GTG CTG GCG CTG CAG CAC GAG
GTG CTG CCG AAG ACG CTG CAT GCG GAG CAG CCG
AGC CCG CAC ATC GCG TGG GAG GGG AGC GGG CTG
TCA TTG CTG CAA GAG GCG CGT CCG TGG CGG CGC
    AAC GGC CGG GTC CGT CGT GCC GGC GTG
```

7. A polyketide synthase comprising a ketosynthase domain wherein said ketosynthase domain comprises a peptide sequence selected from the group consisting of

39

(a) Phe-Phe-Gly-Cys-Gln-Ala-Glu-Arg-Ala-Arg-(subset of SEQ ID NO:5);
(b) Ala-Gly-Pro-Arg-Val-Ala-Gly-Met-Leu-Leu-(subset of SEQ ID NO:5);
(c) Leu-Lys-Ala-Ala-Val-Xaa-Arg-Ala-Ala-Arg-(subset of SEQ ID NO:5);
(d) Arg-Arg-Pro-Cys-Ala-Gly-Val-Ile-Arg-Gly-(subset of SEQ ID NO:5);
(e) Ser-Ala-Val-Asn-Gln-Asn-Val-Ala-Ala-Arg-(subset of SEQ ID NO:5);
(f) Phe-Xaa-Trp-Arg-Arg-Thr-Ala-Leu-Pro-Ser-(subset of SEQ ID NO:5);
(g) Ser-Gly-Xaa-Ser-Gly-Arg-Ala-Leu-Ser-Ser-(subset of SEQ ID NO:5);
(h) Cys-Gly-Leu-Ser-Pro-Glu-Asp-Ile-Asp-Ala-(subset of SEQ ID NO:5);
(i) Gly-Asp-Pro-Ile-Glu-Ala-Gly-Ala-Leu-Ala-(subset of SEQ ID NO:5);
(j) Glu-Val-Phe-Gly-Pro-Glu-Arg-Ser-Pro-Glu-(subset of SEQ ID NO:5);
(k) Arg-Pro-Leu-Tyr-Leu-Gly-Ser-Ser-Lys-Ser-(subset of SEQ ID NO:5);
(l) Asn-Leu-Gly-His-Ala-Gln-Ala-Ala-Ala-Gly-(subset of SEQ ID NO:5);
(m) Val-Ala-Gly-Val-Ile-Lys-Met-Val-Leu-Ser-(subset of SEQ ID NO:5);
(n) Met-Gln-His-Glu-Val-Leu-Pro-Lys-Thr-Leu-(subset of SEQ ID NO:5);
(o) His-Ala-Glu-Gln-Pro-Ser-Pro-His-Ile-Gly-(subset of SEQ ID NO:5);
(p) Trp-Glu-Gly-Ser-Gly-Leu-Ser-Leu-Leu-Gln-(subset of SEQ ID NO:5);
(q) Glu-Ala-Arg-Pro-Trp-Arg-Arg-Asn-Gly-Arg-(subset of SEQ ID NO:5); and
(r) Val-Arg-Arg-Ala-Gly-Val-Scr-Ser-Phe-Gly-Ile-Ser-Gly-Thr-Asn-Ala-His-(subset of SEQ ID NO:5).

8. The polyketide synthase defined in claim 7 wherein said ketosynthase domain includes the peptide sequence:

```
                                      (SEQ ID NO:5)
Phe-Phe-Gly-Cys-Gln-Ala-Glu-Arg-Ala-Arg-

Ala-Gly-Pro-Arg-Val-Ala-Gly-Met-Leu-Leu-

Leu-Lys-Ala-Ala-Val-Xaa-Arg-Ala-Ala-Arg-

Arg-Arg-Pro-Cys-Ala-Gly-Val-Ile-Arg-Gly-

Ser-Ala-Val-Asn-Gln-Asn-Val-Ala-Ala-Arg-

Phe-Xaa-Trp-Arg-Arg-Thr-Ala-Leu-Pro-Ser-

Ser-Gly-Xaa-Ser-Gly-Arg-Ala-Leu-Ser-Ser-

Cys-Gly-Leu-Ser-Pro-Glu-Asp-Ile-Asp-Ala-

Val-Glu-Ala-His-Gly-Thr-Gly-Thr-Ser-Leu-

Gly-Asp-Pro-Ile-Glu-Ala-Gly-Ala-Leu-Ala-

Glu-Val-Phe-Gly-Pro-Glu-Arg-Ser-Pro-Glu-

Arg-Pro-Leu-Tyr-Leu-Gly-Ser-Ser-Lys-Ser-

Asn-Leu-Gly-His-Ala-Gln-Ala-Ala-Ala-Gly-

Val-Ala-Gly-Val-Ile-Lys-Met-Val-Leu-Ser-
```

40

-continued

```
Met-Gln-His-Glu-Val-Leu-Pro-Lys-Thr-Leu-

His-Ala-Glu-Gln-Pro-Ser-Pro-His-Ile-Gly-

Trp-Glu-gly-Ser-Gly-Leu-Ser-Leu-Leu-Gln-

Glu-Ala-Arg-Pro-Trp-Arg-Arg-Asn-Gly-Arg-

Val-Arg-Arg-Ala-Gly-Val-Ser-Ser-Phe-Gly-

Ile-Ser-Gly-Thr-Asn-Ala-His-.
```

9. A purified and isolated DNA molecule that comprises an open reading frame of a polyketide synthase, wherein said open reading frame includes an encoding sequence for a ketosynthase domain that comprises:

```
TTC TTC GGT TGC CAG GCG GAA CGG GCG CGG GCT
GGG CCG AGG GTT GCG GGA ATG CTG TTG TTG AAA
GCG GCT GTC TGA CGC GCA GCG CGA CGG CGA CCG
TGT GCT GGG GTG ATC CGT GGC TCT GCG GTG AAC
CAG AAC GTC GCA GCC AGG TTC TGA TGG CGC CGA
ACG GCC CTG CCC AGC AGC GGG TGA TCC GGC AGG
GCG CTG TCG TCG TGT GGT CTG TCG CCC GAG GAC
ATC GAC GCG GTG GAG GCG CAC GGT ACG GGC ACG
AGC CTT GGA GAC CCG ATC GAG GCC GGA GCG CTG
GCG GAG GTG TTT GGA CCG GAG CGT AGC CCC GAG
CTG CCG CTG TAC CTG GGA TCG TCG AAG TCG AAC
CTC GGA CAT GCG CAG GCG GCG GCG GGC GTG GCG
GGC GTG ATC AAG ATG GTG CTG TCG ATG CAG CAC
GAG GTG CTG CCG AAG ACG CTG CAC GCG GAG CAG
CCG AGC CCG CAC ATT GGG TGG GAA GGA AGC GGG
CTG TCG CTG CTG CAA GAG GCG CGT CCG TGG CGG
CGC AAC GGC CGG GTC CGT CGT GCC GGC GTG TCG
    TCG TTC GGG
``` or a continuous subset thereof that encodes at least 10 amino acids.

10. A chimeric polyketide synthase that comprises one or more domains selected from the group consisting of:

(a) the amino acid sequence,

```
                                      (SEQ ID NO:7)
Ala-Leu-Arg-Ala-Trp-Ile-Glu-Arg-Gly-Ala-

Pro-Thr-Pro-Val-Arg-Val-Val-Ile-Asp-Thr-

Asn-Ala-Ala-Ser-Ser-Pro-Arg-Ser-Asp-Val-

Ala-Gly-Ser-Ser-His-Glu-Ala-Thr-Arg-Gln-

Ala-Leu-Ser-Leu-Leu-Gln-Ala-Trp-Leu-Ser-

Glu-Pro-Arg-Leu-Asp-Ala-Val-Xaa-Leu-Val-

Trp-Val-Thr-Arg-Gly-Ala-Val-Ser-Ala-Ala-

Pro-Asp-Asp-Ala-Val-Xaa-Asp-Leu-Ala-His-

Gly-Pro-Leu-Trp-Gly-Leu-Ile-Arg-Thr-Ala-

Arg-Ser-Glu-His-Pro-Glu-Arg-Arg-Leu-Arg-

Leu-Ile-Asp-Val-Gly-Thr-Xaa-Pro-Val-Asp-

Thr-Gly-Leu-Leu-Ala-Xaa-Ala-Leu-Ala-Thr-

Ala-Ala-Glu-Pro-Glu-Leu-Ala-Leu-Pro-Arg-

Gly-Pro-Xaa-Trp-Pro-Pro-Ala-Gly-Ser-Xaa-
```

Xaa-Pro-His-Arg-Lys-Thr-His-Pro-Thr-Pro-

Arg-Leu-Asp-Leu-Pro-Ala-Pro-Xaa-Cys-Xaa-

Xaa-Asn-Leu-Gly-Arg-Leu-Gly-Xaa-Ala-Xaa-

Asn-Pro-Ser-Cys-Ser-Pro-Xaa-Arg-Val-Xaa-

Ala-Pro-Phe-Ser-Xaa-Leu-Pro-Pro-Gly-Ala-

Xaa-Ser-Pro-Arg-Ala-Pro-Asn-Phe-Ser-Ile-

Leu-Gln-Glu-Xaa-Ala-Pro-Lys-Pro-Phe-Asn-

Val-Ala-Ser-Ile-Phe-Asn-Arg-Lys-Asn-Ser-

Pro-Xaa-Cys-Arg-Ile-Xaa-Pro-Ala-Pro-Leu-

Thr-Val-Leu-Pro-Arg-Xaa-Val-Ser-Xaa-Gly-

Phe-Gln-Thr-Lys-Pro-Thr-Xaa-Cys-Leu-Ala-

Lys-Val-Arg-Ala-Pro-Leu-Xaa-Ile-Thr-Asn-, or a subset thereof comprising 10 consecutive amino acids thereof;

(b) the amino acid sequence, (SEQ ID NO:8)
Thr-Lys-Leu-Arg-Pro-Lys-Pro-Xaa-Xaa-Arg- Val-Thr-Thr-Gly-Phe-Phe-Val-Gly-Phe-Xaa- Arg-Lys-Leu-Xaa-Gly-Xaa-Xaa-Gln-Glu-Arg- His-Xaa-Leu-Glu-Xaa-Asp-Xaa-Ala-Gly-Arg- Leu-Gly-Lys-Xaa-Ser-Xaa-Leu-Xaa-Lys-Xaa- Ser-Asn-Arg-Glu-Pro-Trp-Xaa-Xaa-Glu-Val- Asn-Leu-Gly-Xaa-Arg-Lys-Val-Arg-Ala-Xaa- Asn-Arg-Val-Phe-Lys-Met-Cys-Cys-Ser-Met- Gln-His-Glu-Xaa-Leu-Pro-Lys-Thr-Xaa-Arg- Arg-Ser-Ser-Xaa-Ala-Gly-His-Trp-Trp-Arg- Glu-Arg-Ala-Phe-Val-Ala-Ala-Arg-Gly-Ala- Ser-Val-Ala-Ala-Gln-Arg-Pro-Gly-Ala-Ala- Arg-Gly-Arg-Val-Val-Val-Arg-Ile-Ser-Gly- Thr-Asn-Ala-His-Val-Ile-Leu-Glu-Glu-Ala- Pro-Val-Glu-Ala-Ala-Arg-Glu-Pro-Val-Glu- Ala-Val-Arg-Glu-Pro-Val-Glu-Ala-Glu-Gly- Val-Ala-Ile-Pro-Leu-Leu-Leu-Ser-Gly-Arg- Asp-Glu-Ala-Ser-Val-Ala-Ala-Gln-Ala-Gly- Arg-Trp-Ala-Lys-Trp-Leu-Glu-Glu-His-Gly- Glu-Val-Gly-Trp-Ser-Asp-Val-Val-Arg-Thr- Ala-Ala-Leu-His-Arg-Thr-His-Phe-Glu-Ser- Arg-Ala-Ser-Val-Leu-Ala-Ala-Ser-Ala-Ala- Gly-Ala-Val-Glu-Gly-Leu-Arg-Ala-Leu-Ser- Ser-Gly-Arg-Pro-Asp-Ala-Ala-Val-Val-Ser- -continued Gly-Thr-Ala-Lys-Arg-Gly-Gly-Lys-Leu-, or a subset thereof comprising 10 consecutive amino acids thereof;

(c) the amino acid sequence, (SEQ ID NO:9)

Lys-Leu-Ala-Val-Leu-Phe-Thr-Gly-Gln-Gly-
Ser-Gln-Arg-Leu-Gly-Met-Gly-Lys-Arg-Leu-
Tyr-Glu-Val-Tyr-Pro-Val-Phe-Arg-Ala-Ala-
Phe-Asp-Glu-Val-Cys-Glu-Ala-Leu-Asp-Ala-
His-Leu-Asp-Arg-Gly-Leu-Arg-Xaa-Val-Val-
Phe-Ala-Ala-Ala-Gly-Ser-Glu-Glu-Xaa-Ala-
Gln-Leu-Glu-Arg-Thr-Glu-Tyr-Thr-Gln-Pro-
Gly-Leu-Phe-Ala-Leu-Glu-Val-Ala-Leu-Tyr-
Arg-Gln-Trp-Xaa-Ser-Trp-Gly-Leu-Asn-Pro-
Leu-Arg-Cys-Trp-Gly-Thr-Arg-Xaa-Glu-Xaa-
Xaa-Thr-Leu-Arg-Thr-Xaa-Arg-Val-Xaa-Xaa-
Pro-Xaa-Ser-Ala-Asp-Gln-Gly-Phe-Gln-Xaa-
Arg-Gly-Thr-Met-Phe-Pro-Xaa-Lys-Pro-Pro-
Asn-Pro-Lys-Xaa-Thr-Gly-Xaa-Ser-Lys-Ser-
Gly-Gln-Gly-His-Xaa-Leu-Pro-Gly-Xaa-Pro-
Pro-Ser-Thr-Ser-Asn-Xaa-Thr-Asn-Ala-Phe-
Xaa-Val-Ala-His-Ala-Glu-Pro-Gly-Arg-Pro-
Pro-Leu-Ser-Phe-Xaa-Leu-Pro-Pro-His-Xaa-
Glu-Xaa-Lys-Ile-Glu-Val-Pro-Ile-Leu-Pro-
Pro-Leu-Arg-Val-Pro-Xaa-Ala-Pro-Cys-Lys-
Thr-Asn-Xaa-Ile-Val-Asp-Xaa-Xaa-Gly-Pro-
Lys-Asn-, (d) the amino acid sequence, (SEQ ID NO:10)

Gly-Lys-Xaa-Xaa-Xaa-Leu-Val-Lys-Phe-Ala-
Xaa-Ile-Phe-Gly-Asn-Ala-Gly-Gly-Asp-Phe-
Val-Gly-Pro-Asn-Arg-Gly-Gly-Cys-Leu-Val-
Xaa-Xaa-His-Arg-Thr-Gly-Arg-Asn-Xaa-Xaa-
Gly-Gln-Xaa-Glu-Gly-Val-Xaa-Arg-Arg-Thr-
Leu-Pro-Leu-Pro-Gly-Val-Asp-Glu-Leu-Xaa-
Xaa-Ala-His-Ser-Xaa-Xaa-Gly-Gly-Xaa-Asp-
Phe-Ser-Gly-Phe-Thr-Arg-Val-Asp-Glu-Val-
Ile-Arg-Leu-Arg-Pro-Ala-Phe-Gln-Gly-Leu-
Trp-Ser-Xaa-Arg-Xaa-Xaa-Thr-Asp-Phe-Phe-
Arg-Pro-Gly-Val-Phe-Ala-Gln-Arg-Arg-Asp-

-continued

```
Glu-Gln-Arg-Arg-Gly-Leu-Arg-Val-His-Pro-
Ala-Xaa-Met-Asn-Xaa-Ala-Leu-His-Thr-Met-
Phe-Ala-Phe-Ala-Glu-Val-Ser-Ala-Pro-
Xaa-Asp-Val-Leu-Leu-Xaa-Phe-Ser-Cys-Ser-
Xaa-Val-Ala-Leu-His-Ala-Thr-Gly-Ala-Ser-
Glu-Xaa-Arg-Val-Arg-Leu-Glu-Xaa-Ala-Gly-
Gly-Arg-Asp-Ser-Ala-Gln-Ala-Ala-Ser-
Leu-Arg-Val-Thr-Asp-Ala-Ala-Gly-Gln-Pro-
Val-Val-Ser-Val-Gly-Ala-Leu-His-Leu-Arg-
Arg-Ala-Thr-Ala-Glu-Gln-Leu-Arg-Ala-Ala-
Thr-His-Ala-Glu-Ala-Gln-His-Leu-Tyr-Arg-
Val-Asp-Phe-Gln-Leu-Val-Ser-Leu-Val-Glu-
Ala-Gly-Ser-Lys-Val-Asp-Ser-Leu-Val-Val-
Leu-Arg-Ala-Pro-Glu-Gly-Arg-Gly-Arg-Leu-
Gly-Glu-Ala-Leu-Gly-Val-Glu-Ala-Ile-Ala-
Gly-Leu-Asp-Ala-,
``` or a subset thereof comprising 10 consecutive amino acids thereof;

(e) the amino acid sequence,

```
                                    (SEQ ID NO:5)
Phe-Phe-Gly-Cys-Gln-Ala-Glu-Arg-Ala-Arg-
Ala-Gly-Pro-Arg-Val-Ala-Gly-Met-Leu-Leu-
Leu-Lys-Ala-Ala-Val-Xaa-Arg-Ala-Ala-Arg-
Arg-Arg-Pro-Cys-Ala-Gly-Val-Ile-Arg-Gly-
Ser-Ala-Val-Asn-Gln-Asn-Val-Ala-Ala-Arg-
Phe-Xaa-Trp-Arg-Arg-Thr-Ala-Leu-Pro-Ser-
Ser-Gly-Xaa-Ser-Gly-Arg-Ala-Leu-Ser-Ser-
Cys-Gly-Leu-Ser-Pro-Glu-Asp-Ile-Asp-Ala-
Val-Glu-Ala-His-Gly-Thr-Gly-Thr-Ser-Leu-
Gly-Asp-Pro-Ile-Glu-Ala-Gly-Ala-Leu-Ala-
Glu-Val-Phe-Gly-Pro-Glu-Arg-Ser-Pro-Glu-
Arg-Pro-Leu-Tyr-Leu-Gly-Ser-Ser-Lys-Ser-
Asn-Leu-Gly-His-Ala-Gln-Ala-Ala-Ala-Gly-
Val-Ala-Gly-Val-Ile-Lys-Met-Val-Leu-Ser-
Met-Gln-His-Glu-Val-Leu-Pro-Lys-Thr-Leu-
His-Ala-Glu-Gln-Pro-Ser-Pro-His-Ile-Gly-
Trp-Glu-Gly-Ser-Gly-Leu-Ser-Leu-Leu-Gln-
Glu-Ala-Arg-Pro-Trp-Arg-Arg-Asn-Gly-Arg-
Val-Arg-Arg-Ala-Gly-Val-Ser-Ser-Phe-Gly-
Ile-Ser-Gly-Thr-Asn-Ala-His-,
```

(f) the amino acid sequence,

```
                                    (SEQ ID NO:3)
Asp-Thr-Ala-Cys-Ser-Ser-Ser-Leu-Val-Ser-
Leu-His-Leu-Ala-Cys-Thr-Ala-Leu-Arg-Gln-
Gly-Glu-Cys-Asp-Leu-Ala-Leu-Thr-Gly-Gly-
Val-Met-Val-Ile-Thr-Thr-Pro-Ala-Gly-Phe-
Val-Xaa-Phe-Ser-Arg-Ala-Arg-Gly-Leu-Ala-
Arg-Asp-Gly-Arg-Cys-Lys-Ser-Phe-Ser-Ala-
Gln-Ala-Asp-Gly-Val-Ile-Trp-Ser-Glu-Gly-
Cys-Gly-Met-Leu-Leu-Lys-Arg-Leu-Ser-
Asp-Ala-Arg-Arg-Asp-Arg-Asp-Arg-Val-Leu-
Gly-Val-Ile-Arg-Gly-Ser-Ala-Val-Asn-Gln-
Asp-Arg-Arg-Ser-Gln-Gly-Leu-Thr-Ala-Pro-
Asn-Gly-Pro-Ala-Gln-Gln-Arg-Val-Ile-Arg-
Gln-Ala-Leu-Ser-Ser-Cys-Gly-Leu-Ser-Pro-
Glu-Asn-Arg-Arg-Gly-Gly-Gly-Ala-Trp-Asp-
Gly-Thr-Ser-Leu-Gly-Asp-Pro-Ile-Glu-Ala-
Gly-Ala-Leu-Ala-Glu-Val-Phe-Gly-Pro-Glu-
Arg-Ser-Pro-Glu-Arg-Pro-Leu-Tyr-Leu-Gly-
Ser-Ser-Lys-Ser-Asn-Leu-Gly-His-Ala-Gln-
Ala-Ala-Ala-Gly-Val-Ala-Gly-Val-Ile-Lys-
Met-Val-Leu-Ala-Leu-Gln-His-Glu-Val-Leu-
Pro-Lys-Thr-Leu-His-Ala-Glu-Gln-Pro-Ser-
Pro-His-Ile-Ala-Trp-Glu-Gly-Ser-Gly-Leu-
Ser-Leu-Leu-Gln-Glu-Ala-Arg-Pro-Trp-Arg-
Arg-Asn-Gly-Arg-Val-Arg-Arg-Ala-Gly-Val-
Ser-Ser-Phe-Gly-Ile-Ser-Gly-Thr-Asn-Ala-,
```

(g) the amino acid sequence,

```
                                    (SEQ ID NO:1)
Thr-Leu-Gly-Ala-Leu-Val-Ala-Arg-Arg-Leu-
Val-Asp-Arg-His-Gly-Val-Lys-His-Leu-Val-
Leu-Leu-Ser-Arg-Arg-Gly-Pro-Asp-Ala-Pro-
Gly-Ala-Ser-Asp-Leu-Ala-Ala-Glu-Leu-Gln-
Ala-Arg-Gly-Ala-Ser-Val-Val-Val-Ala-Ala-
Ala-Asp-Ala-Ala-Asp-Arg-Val-Ala-Leu-Glu-
Arg-Val-Leu-Leu-Ala-Ile-Pro-His-Asp-Arg-
Pro-Leu-Thr-Ala-Val-Val-His-Ala-Ala-Gly-
Thr-Leu-Asp-Asp-Gly-Val-Leu-Ser-Ser-Met-
Thr-Pro-Ala-Arg-Leu-Ser-Ala-Val-Leu-Arg-
Ala-Lys-Val-Asp-Ala-Ala-Val-Asn-Leu-Asp-
Glu-Gln-Thr-Arg-His-Ser-Pro-Leu-Arg-Ala-
```

Phe-Val-Leu-Phe-Ser-Ser-Leu-Ser-Gly-Val-Leu-Gly-Ser-Pro-Ala-Gln-Ser-Asn-Tyr-Ala-Ala-Ala-,

11. A purified and isolated DNA molecule encoding a polyketide synthase domain which comprises a sequence selected from the group consisting of:

(a) SEQ ID NO:2;
(b) SEQ ID NO:4;
(c) SEQ ID NO:6;
(d)

```
ATGCATTGCGCGCTTGGATC      (SEQ ID NO:11);
GAGCGGGGCGCGCCAACGCC
TGTGCGGGTGGTGATCGACA
CGAACGCTGCCAGCTCACCG
CGCTCGGACGTGGCGGGGTC
GTCGCACGAGGCGACGAGGC
AGGCGCTGTCGCTGCTGCAA
GCGTGGTTGTCGGAGCCGCG
GCTCGACGCTGTCGANCTGG
TGTGGGTGACGCGGGGCGCG
GTCAGCGCAGCTCCGGACGA
CGCCGTCGANGACCTGGCGC
ACGGGCCGCTGTGGGGGCTT
ATTCGCACGGCGCGCAGCGA
GCACCCCGAGCGCCGGCTGC
GCTTGATCGATGTGGGGACC
GANCCCGTGGACACTGGGCT
GCTGGCGCNGGCGCTGGCGA
CGGCGGCGGAACCNGAACTT
GCCCTGCCCCGGGCCCGTN
CTGGCCCCCCGCTGGTTCCN
TACNGCCGCACCGAAAAACT
CACCCAACCCCCCGGCTGGA
CCTTCCGGCACCTNCTTGTT
NACNGAACCTTGGCCGTCTT
GGGCNAGCGTNAAACCCNTC
TTGTTCCCCCNCNCGGGTTT
AAGCACCTTTTTCTNAACTT
CCCCCCGGGGCCTGAAGCCC
CCGGGCCCCCAACTTTTCAA
TCCTCCAAGAAANCGCCCCA
AAACCTTTCAATGTTGCTTC
AATTTTCAACCGGAAAAATT
CCCCCTTNTGCCGGATTAAN
CCGGCCCCCCTAACCGTTCT
NCCCCGCTNGGTTTCAAANG
GTTTTCAAACNAAGCCAACC
NCTTGTTTGGCCAAGGTAAG
GGCNCCCCTCCNAATAACGA
ACGNTTN,
```

(e)

```
TGNACCAAGCTAAGGCCGAA      (SEQ ID NO:12)
GCCCNGCANNAGGGTAACNA
CAGGCTTTTTTGTNGGTTTT
NCCCGAAAATTAANGGGNGN
GGNNCAGGAACGGCACNCCC
TNGAANTCGATTGAGCCGGA
CGNTTGGGGAAGNTTTCGGN
CTTGGNCAAGCNGAGCAACC
GTGAACCTTGGTTNNTGGAA
GTGAACCTTGGCANGCGCAA
GGTTCGGGCGGNTAACCGGG
TGTTCAAGATGTGCTGTTCG
ATGCAGCACGAGNTGCTGCC
GAAGACGTGNAGGCGGAGCA
GCNGAGCCGGNCATTGGTGG
AGGGAGCGGGCTTTCGTTGC
TGCAAGAGGCGCGTCCGTGG
CGGCGCAACGGCCGGGCGCG
GCGCGCGGGCGTGTCGTCGT
TCGGATCAGCGGGACGAACG
CCCATGTCATCCTCGAAGAG
GCGCCGGTGGAGGCGGCTCG
CGAGCCGGTGGAGGCGGTGC
GCGAGCCGGTGGAGGCGGAG
GGTGTTGCGATACCGCTGTT
GCTGTCGGGGCGAGACGAGG
CCTCGGTGGCGGCGCAGGCG
GGGCGGTGGGCGAAGTGGCT
```

```
GGAAGAGCACGGGGAGGTGG
GGTGGTCGGACGTGGTGAGG
ACGGCGGCGCTGCACCGGAC
GCACTTCGAGTCGCGGGCGT
CGGTGCTTGCGGCGAGCGCT
GCGGGAGCTGTGGAGGGTCT
TCGCGCGCTGTCGTCGGGGC
GGCCGGATGCGGCGGTGGTG
AGCGGGACGGCGAAGCGAGG
CGGGAAGCTT,
```

(f)

```
AAGCTTGCGGTGCTGTTCAC    (SEQ ID NO:13)
GGGGCAGGGCAGCCAGCGGC
TCGGGATGGGGAAGAGGCTT
TACGAAGTGTACCCCGTGTT
CCGTGCGGCGTTCGACGAGG
TGTGCGAGGCGCTGGACGCG
CATCTCGACCGTGGGTTGAG
AGANGTGGTGTTCGCGGCCG
CGGGCAGCGAGGAANGAGCG
CAGCTGGAGCGGACGGAGTA
CACGCAGCCCGGGCTGTTTG
CGCTGGAAGTGGCGCTGTAC
CGTCAGTGGGANTCGTGGGG
GCTGAACCCGCTGCGCTGCT
GGGGCACTCGATANGAAANC
TGAACGCTGCGCACGTNGCG
GGTNTNCTGANCCTTGCGGA
CGCAGCNAACTANTGTNCCC
CCGCNGTCNGCTGATCAAGG
GTTCCAAGNCCGGGAACCA
TGTTTCCGTNGAAGCCTCCG
AACCCGAAGTNCACCGGCNC
TTCGAAGTCNGGCCAGGGCC
ACNAACTCCCCGGCTAACCC
CCATCCACGTCTAACNGGAC
AAACGCGTTCNCCGTTGCCC
ACGCTGAGCCCGGCCGCCCC
CCGCTTTCTTTTNCCCTTCC
ACCCCATNACGAACNGAAAA
TCGAAGTCCCGATTCTTCCC
CCCCTGCGTGTACCNTANGC
ACCCTGCAAAACCAATTNCA
TTGTTGATTNCAANGGCCCC
AAGAACC, and
```

(g)

```
NGGCAAGNGCNGGGNTTTGG    (SEQ ID NO:14)
TTAAATTCGCCCNTATTTTC
GGAAATGCCGGGGGTGATTT
TGTTGGGCCCAACCGGGGNG
GGTGTTTGGTTNAANACCAC
CGNACAGGACGGAATNCCCN
TGGTCAANAGGAAGGGGTTT
NACGAAGAACCTTGCCACTT
CCGGGAGTTGATGAGCTAAN
ANTTGCCCATTCCNGGCNCG
GAGGCGNTGACTTTTCGGGT
TTTACGAGGGTTGATGAGGT
GATTCGGTTACGCCCGGCCT
TCCAGGGTTTGTGGAGCTNT
CGNNTCGANACGGACTTTTT
TCGCCCGGGTGTTTTTGCCC
AAAGACGGGACGAACAGCGC
CGAGGATTACGGGTGCATCC
GGCGNTGATGAACNCCGCGT
TGCATACGATGTTCGCAGCG
TTTGCGGAGGTATCAGCGCC
GGANGACGTGCTGCTGCNTT
TTTCGTGTTCGGANGTGGCG
TTGCACGCCACGGGGCGAG
CGAGNTCCGGGTGAGGCTGG
AGNTCGCAGGAGGCAGAGAC
TCGGCACAGGCAGCCGCNTC
GCTGCGCGTTACAGATGCCG
CCGGCCAGCCGGTGGTGAGC
GTCGGTGCCCTGCATCTGCG
CGGGCGACGGCCGAGCAGCT
GCGGGCAGCGACGCATGCCG
```

-continued

```
AGGCGCAGCACCTGTACCGG

GTGGACTTCCAGCTCGTGAG

CCTCGTGGAGGCGGGCTCGA

AGGTGGACTCGCTGGTGGTG

CTCCGTGCGCCTGAGGGGCG

AGGGCGACTGGGCGAAGCGC

TGGGTGTGGAGGCGATCGCA

GGCCTCGATGCAT,
```

12. A polynucleotide that is complementary to a nucleotide sequence (a) to (h) of claim 11.

13. A recombinant expression system capable, when inserted into a host cell, of expressing a nucleotide sequence encoding the polyketide synthase domain of claim 1, wherein said encoding sequence is operably linked to control sequences effective in said cell.

14. A host cell modified to contain a recombinant expression system according to claim 13.

15. A recombinant expression system capable, when inserted into a host cell, of expressing a nucleotide sequence encoding the polyketide synthase domain of claim 4, wherein said encoding sequence is operably linked to control sequences effective in said cell.

16. A host cell modified to contain a recombinant expression system according to claim 15.

17. A recombinant expression system capable, when inserted into a host cell of expressing a nucleotide sequence encoding the polyketide synthase domain of claim 7, wherein said encoding sequence is operably linked to control sequences effective in said cell.

18. A host cell modified to contain a recombinant expression system according to claim 17.

19. A recombinant expression system capable, when inserted into a host cell, of expressing a nucleotide sequence encoding the chimeric polyketide synthase domain of claim 10, wherein said encoding sequence is operably linked to control sequences effective in said cell.

20. A host cell modified to contain a recombinant expression system according to claim 19.

21. A method to prepare a polyketide synthase domain comprising culturing the cell of claim 14 under conditions wherein said polyketide synthase domain is expressed.

22. A method to prepare a polyketide synthase domain comprising culturing the cell of claim 16 under conditions wherein said polyketide synthase domain is expressed.

23. A method to prepare a polyketide synthase domain comprising culturing the cell of claim 18 under conditions wherein said polyketide synthase domain is expressed.

24. A method to prepare a polyketide synthase domain comprising culturing the cell of claim 20 under conditions wherein said polyketide synthase domain is expressed.

* * * * *